(12) United States Patent
Kobilka et al.

(10) Patent No.: US 10,556,919 B2
(45) Date of Patent: Feb. 11, 2020

(54) LIMONENE-BASED, NON-HALOGENATED FLAME RETARDANTS FOR POLYMERIC APPLICATIONS

(71) Applicant: International Business Machines Corporation, Armonk, NY (US)

(72) Inventors: Brandon M. Kobilka, Tucson, AZ (US); Jason T. Wertz, Pleasant Valley, NY (US); Scott B. King, Rochester, MN (US); Joseph Kuczynski, North Port, FL (US)

(73) Assignee: International Business Machines Corporation, Armonk, NY (US)

( * ) Notice: Subject to any disclaimer, the term of this patent is extended or adjusted under 35 U.S.C. 154(b) by 144 days.

(21) Appl. No.: 15/830,713

(22) Filed: Dec. 4, 2017

(65) Prior Publication Data

US 2019/0169213 A1  Jun. 6, 2019

(51) Int. Cl.
*C07F 9/146* (2006.01)
*C07F 9/655* (2006.01)
(Continued)

(52) U.S. Cl.
CPC ............ *C07F 9/146* (2013.01); *C07F 9/3217* (2013.01); *C07F 9/4015* (2013.01); *C07F 9/65502* (2013.01); *C07F 9/65505* (2013.01); *C07F 9/65515* (2013.01); *C08G 64/0258* (2013.01); *C08G 64/302* (2013.01); *C08J 3/203* (2013.01); *C08K 5/5313* (2013.01); *C08K 5/5333* (2013.01); *C08K 5/5337* (2013.01); *C08K 5/5373* (2013.01); *H01L 23/293* (2013.01); *H01L 24/29* (2013.01); *C08J 2369/00* (2013.01); *H01L 2224/2919* (2013.01)

(58) Field of Classification Search
CPC ........ C07F 9/3217; C07F 9/02; C07F 9/3276; C07F 9/3288
See application file for complete search history.

(56) References Cited

U.S. PATENT DOCUMENTS

2019/0185497 A1\* 6/2019 Kobilka ................ C07F 9/3276

FOREIGN PATENT DOCUMENTS

WO      2017096187 A1    6/2017

OTHER PUBLICATIONS

Itoh (Stereochemical Studies on the Nucleophilic Substitution in the Reaction of Allylic Phosphates with Organoaluminum Reagents. Bull. Chem. Soc. Jpn., 1980, 53, pp. 2357-2362).\*

(Continued)

*Primary Examiner* — Brieann R Johnston
(74) *Attorney, Agent, or Firm* — Patterson + Sheridan, LLP

(57) ABSTRACT

A limonene-based flame-retardant compound, a method of making a flame-retardant polymer, and an article of manufacture comprising a material that includes a limonene-based flame-retardant compound. In an embodiment, the method includes forming a limonene-based derivative; forming a phosphorus-based flame-retardant molecule; reacting the limonene-based derivative with the phosphorus-based flame-retardant molecule to form a limonene-based flame-retardant compound; and forming a flame-retardant polymer from the limonene-based flame-retardant compound. In some embodiments, the limonene-based flame-retardant compound has variable functionality including vinyl, epoxide, methylene bridges, and thioethers.

16 Claims, 11 Drawing Sheets

(51) Int. Cl.

| | |
|---|---|
| *C07F 9/40* | (2006.01) |
| *C07F 9/32* | (2006.01) |
| *C08G 64/30* | (2006.01) |
| *C08K 5/5337* | (2006.01) |
| *C08K 5/5373* | (2006.01) |
| *C08K 5/5333* | (2006.01) |
| *C08K 5/5313* | (2006.01) |
| *C08J 3/20* | (2006.01) |
| *C08G 64/02* | (2006.01) |
| *H01L 23/29* | (2006.01) |
| *H01L 23/00* | (2006.01) |

(56) References Cited

OTHER PUBLICATIONS

Keeney (Reaction of Terpenes with Diethyl Phosphonate under Free Radical Conditions. J. Org. Chem., 1974, 39(5), pp. 682-686).*

Lira (One-pot Synthesis of organophosphate monoesters from alcohols. Tetrahedron Letters. 2013, 54, pp. 1690-1692).*

Eummer (Novel Limonene Phosphonate and Farnesyl Diphosphate Analogues: Design, Synthesis, and Evaluation as Potential Protein-Farnesyl Transferase Inhibitors. Bioorganic & Medical Chemistry, 1999, 7, pp. 241-250).*

Battiste (Reaction of $\alpha$-Pinene and $\beta$-pinene with diethyl hydrogen phosphite Under Free Radical Conditions. Synthetic Communications, 14(11), 1984, pp. 993-1000).*

Ranaweera, C. K., et al., "Biobased Polyols Using Thiol-Ene Chemistry for Rigid Polyurethane Foams with Enhanced Flame-Retardant Properties," J. Renew. Mater (2017), 12 pages.

Mao, Wei, et al., "Design, Preparation and Properties of Novel Flame Retardant Thermosetting Vinyl Ester Copolymers Based on Castor Oil and Industrial Dipentene," Polish Journal of Chemical Technology, vol. 19, No. 3, 8 pages.

* cited by examiner

LIMONENE-BASED, NON-HALOGENATED FLAME RETARDANTS FOR POLYMERIC APPLICATIONS

BACKGROUND

The present disclosure relates to bio-renewable flame-retardant compounds and, more specifically, limonene-based flame-retardant small molecules that can be blended into polymeric materials.

Bio-based, sustainable compounds can be used in the syntheses of substances that previously required petroleum-based raw materials. Examples of uses for bio-based compounds include polymers, cross-linkers, and flame retardants. Limonene (1-Methyl-4-(1-methylethenyl)-cyclohexene) is an example of a bio-based compound.

Typically for polymer applications, most manufacturers work on blending of petroleum-based polymers and bio-based polymer(s) to increase bio-content in the polymer composite. While the bio-content of the blend is higher than the petroleum-based polymer alone, the blends frequently have material properties that are less desirable than those of the petroleum-based polymer alone, or of blends of petroleum-based polymers. Moreover, material properties of 100% bio-based polymers are often unsatisfactory (e.g., PLA is extremely brittle when used by itself). There is a need for bio-based flame-retardant polymers that have the added benefit of including and/or increasing bio-content claims for the composite material. In addition, there is a need to increase bio-based content in polymers without sacrificing materials properties as can be common with 100% bio-based polymers.

SUMMARY

According to an embodiment, limonene-based flame-retardant compounds are provided. The limonene-based flame-retardant compounds are represented by formulas (A)-(G):

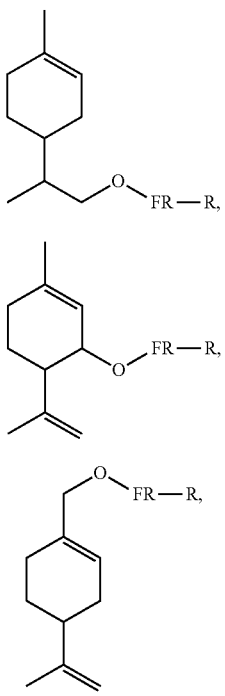

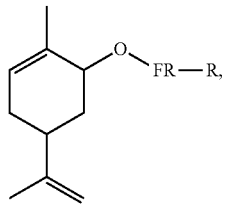

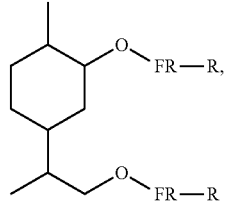

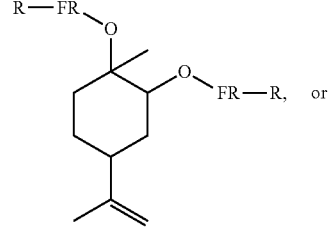

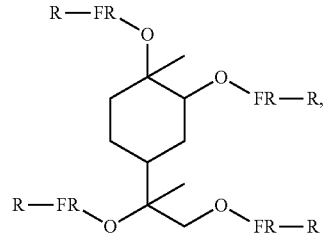

wherein: each FR—R includes a phosphate group or a phosphonate group.

According to another embodiment, a method of forming a limonene-based flame-retardant polymer is provided. The method includes forming a limonene-based derivative; forming a phosphorus-based flame-retardant molecule; reacting the limonene-based derivative with the phosphorus-based flame-retardant molecule to form a limonene-based flame-retardant compound; and forming a flame-retardant polymer from the limonene-based flame-retardant compound.

According to another embodiment, an article of manufacture is provided. The article of manufacture includes a material containing a limonene-based flame-retardant polymer.

Features and other benefits that characterize embodiments are set forth in the claims annexed hereto and forming a further part hereof. However, for a better understanding of the embodiments, and of the advantages and objectives attained through their use, reference should be made to the Drawings and to the accompanying descriptive matter.

BRIEF DESCRIPTION OF THE SEVERAL VIEWS OF THE DRAWINGS

So that the manner in which the above recited features of the present disclosure can be understood in detail, a more particular description of the disclosure, briefly summarized above, may be had by reference to embodiments, some of which are illustrated in the appended drawings. It is to be noted, however, that the appended drawings illustrate only exemplary embodiments and are therefore not to be considered limiting of its scope, for the disclosure may admit to other equally effective embodiments.

DETAILED DESCRIPTION

Figure 1:
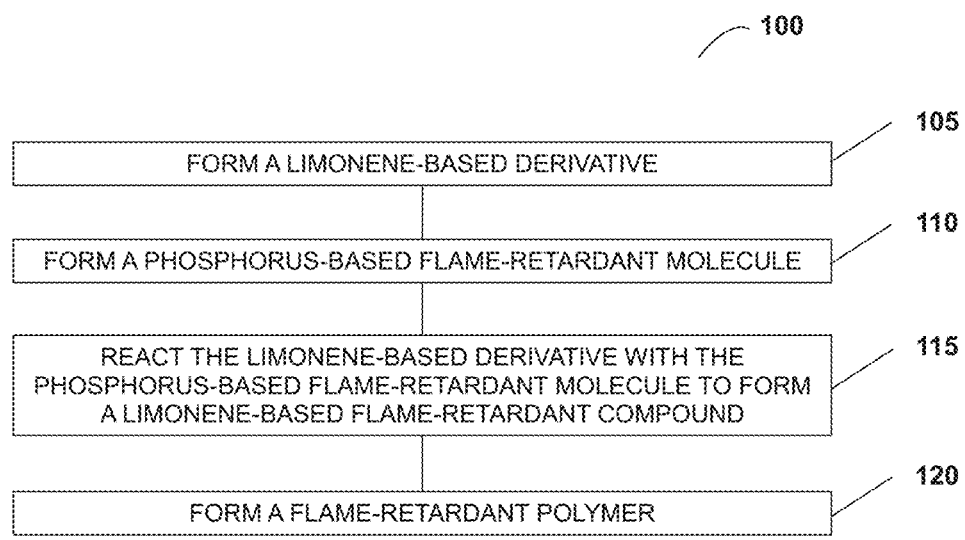
FIG. 1 illustrates a method of forming a limonene-based flame-retardant polymer according to some embodiments.

This disclosure includes chemical structures that show atomic compositions of compounds and relative bonding arrangements of atoms in a chemical compound. Unless specifically stated, the geometric arrangement of atoms shown in the chemical structures is not intended to be an exact depiction of the geometric arrangement of every embodiment, and those skilled in the chemical arts will recognize that compounds may be similar to, or the same as, the illustrated compounds while having different molecular shapes or conformations. For example, the structures denoted herein may show bonds extending in one direction, while embodiments of the same compound may have the same bond extending in a different direction. Additionally, bond lengths and angles, Van der Waals interactions, isoelectronic structures, and the like may vary among instances of the same chemical compound. Additionally, unless otherwise noted, the disclosed structures cover all stereoisomers, conformers, rotamers, isomers, and enantiomers of the represented compounds.

Numbered chemical structures are numbered using numbers, or numbers and letters, in parentheses. Unless otherwise noted, chemical reactions are performed at ambient conditions or under slight heating with no special atmosphere or head space, and may be performed using standard organic solvents to manage mix properties such as viscosity and flow index. Standard procedures for quenching the reaction, solvent removal, and purification are performed.

Bio-based compounds are increasingly being used in the syntheses of substances that previously required petroleum-based raw materials. One benefit of bio-based compounds is that they are from renewable resources. Therefore, these compounds have applications in sustainable, or "green," materials. Sustainable materials are becoming more and more prevalent, due to the rising costs of fossil fuels and increasing environmental regulatory controls. Advances in biotechnology have provided numerous strategies for efficiently and inexpensively producing bio-based compounds on an industrial scale. Examples of these strategies can be found in fermentation technologies, membrane technologies, and genetic engineering. Biotechnological strategies can include plant-based and microorganism-based approaches. Plant-based approaches can involve obtaining a material directly from a plant, or growing plant tissues or cells that can produce bio-based compounds from various substrates using their own biosynthetic pathways. Microorganism-based approaches involve using native or genetically modified fungi, yeast, or bacteria to produce a desired compound from a structurally similar substrate.

Examples of uses for bio-based compounds include polymers, flame-retardants, crosslinkers, etc. In some examples, bio-based polymers and petroleum-based polymers are blended to form a polymer composite. However, polymers can also be entirely bio-based, or produced from a combination of bio- and petroleum-based monomers. Bio-based compounds can impart flame-retardant properties to bio- and petroleum-based polymers. For example, flame-retardant molecules or cross-linkers can be incorporated into polymers. Additionally, flame-retardant monomers can be polymerized to form flame-retardant polymers.

Limonene (1-Methyl-4-(1-methylethenyl)-cyclohexene) is one example of a bio-based compound that can have applications as a component of various polymers, resins, and monomers.

Limonene is currently produced as a side product from the citrus juice industry. Fully synthetic limonene can be made by Diels-Alder addition of two isoprene units. Limonene can also be produced biosynthetically by the enzyme limonene synthase from the substrate geranyl diphosphate. Limonene can also be produced in bacteria such as $E.\ coli$. Additionally, limonene can be extracted from citrus waste such as peels and juices.

According to the present disclosure, limonene is used as a precursor for flame-retardant compounds. These compounds can include small molecules, cross-linkers, monofunctional molecules, monomers, and polymers. The limonene-based flame-retardant compounds can be added to polymers, fabrics, resins, or other materials during blending, curing, foaming, extrusion, or other processing techniques. In addition to directly adding the limonene-based flame-retardant monomers to the materials during processing, the added limonene-based flame-retardant monomers can be contained within microcapsules.

As used herein, the term "substituted" means that a hydrogen group has been replaced with a heteroatom, or a heteroatom-containing group. For example, a "substituted hydrocarbyl" is a radical made of carbon and hydrogen where at least one hydrogen is replaced by a heteroatom or heteroatom-containing group.

The following abbreviations may be used herein: dme is 1,2-dimethoxyethane, Me is methyl, Et is ethyl, Pr is propyl, cPr is cyclopropyl, nPr is normal propyl, iPr is isopropyl, Bu is butyl, nBu is normal butyl, iBu is isobutyl, sBu is sec-butyl, tBu is tert-butyl, p-tBu is para-tert-butyl, Ph is phenyl, Bn is benzyl (i.e., $CH_2Ph$), Oct is octyl, Cy is cyclohexyl, p-Me is para-methyl, THF (also referred to as thf) is tetrahydrofuran, tol is toluene, and EtOAc is ethyl acetate.

As used herein, "alkoxides" include those where the alkyl group is a $C_1$ to $C_{10}$ hydrocarbyl. The alkyl group may be straight chain, branched, or cyclic. The alkyl group may be saturated or unsaturated. In some embodiments, the alkyl group may include at least one aromatic group.

The terms "alkyl group," "alkyl radical," "alkyl," "hydrocarbyl radical," "hydrocarbyl," and "hydrocarbyl group" are used interchangeably throughout this document. Likewise, the terms "group," "radical," and "substituent" are also used interchangeably in this document. For purposes of this disclosure, "alkyl group" refers to $C_1$-$C_{100}$ radicals, that may be linear, branched, or cyclic, and when cyclic, aromatic or non-aromatic. Examples of such radicals include methyl, ethyl, n-propyl, isopropyl, n-butyl, isobutyl, sec-butyl, tert-butyl, pentyl, iso-amyl, hexyl, octyl cyclopropyl, cyclobutyl, cyclopentyl, cyclohexyl, cyclooctyl, and their substituted analogues. Substituted alkyl radicals are those in which at least one hydrogen atom of the hydrocarbyl radical has been substituted with at least one halogen (such as Br, Cl, F or I) or at least one functional group such as $C(O)R^*$, $C(O)NR^*_2$, $C(O)OR^*$, $NR^*_2$, $OR^*$, $SeR^*$, $TeR^*$, $PR^*_2$, $AsR^*_2$, $SbR^*_2$, $SR^*$, $BR^*_2$, $SiR^*_3$, $GeR^*_3$, $SnR^*_3$, and $PbR^*_3$ (where $R^*$ is independently a hydrogen or hydrocarbyl radical, and two or more $R^*$ may join together to form a substituted or unsubstituted saturated, partially unsaturated or aromatic cyclic or polycyclic ring structure), or where at least one heteroatom has been inserted within a hydrocarbyl ring.

The term "alkenyl" means a straight-chain, branched-chain, or cyclic hydrocarbon radical having one or more double bonds. These alkenyl radicals may be optionally substituted. Examples of suitable alkenyl radicals include ethenyl, propenyl, allyl, 1,4-butadienyl cyclopropenyl, cyclobutenyl, cyclopentenyl, cyclohexenyl, cyclooctenyl, including their substituted analogues.

The term "alkoxy" or "alkoxide" means an alkyl ether or aryl ether radical wherein the term alkyl is as defined above. Examples of suitable alkyl ether radicals include methoxy, ethoxy, n-propoxy, iso-propoxy, n-butoxy, iso-butoxy, sec-butoxy, tert-butoxy, and phenoxyl.

The term "aryl" or "aryl group" includes a $C_4$-$C_{20}$ aromatic ring, such as a six carbon aromatic ring, and the substituted variants thereof, including phenyl, 2-methylphenyl, xylyl, and 4-bromo-xylyl. Likewise, heteroaryl means an aryl group where a ring carbon atom (or two or three ring carbon atoms) has been replaced with a heteroatom, preferably N, O, or S. As used herein, the term "aromatic" also refers to pseudoaromatic heterocycles which are heterocyclic substituents that have similar properties and structures (nearly planar) to aromatic heterocyclic ligands, but are not by definition aromatic; likewise the term aromatic also refers to substituted aromatics.

Where isomers of a named alkyl, alkenyl, alkoxide, or aryl group exist (e.g., n-butyl, iso-butyl, sec-butyl, and tert-butyl) reference to one member of the group (e.g., n-butyl) is intended to include the remaining isomers (e.g., iso-butyl, sec-butyl, and tert-butyl) in the family, unless otherwise specified herein. Likewise, reference to an alkyl, alkenyl, alkoxide, or aryl group without specifying a particular isomer (e.g., butyl) includes all isomers (e.g., n-butyl, iso-butyl, sec-butyl, and tert-butyl).

Where a structure includes an R group, and the R group is defined using a dotted-line bond, the dotted-line bond is what bonds the R group to the structure.

For any particular compound disclosed herein, any general or specific structure presented also encompasses all conformational isomers, regioisomers, and stereoisomers that may arise from a particular set of substituents, unless stated otherwise. Similarly, unless stated otherwise, the general or specific structure also encompasses all enantiomers, diastereomers, and other optical isomers whether in enantiomeric or racemic forms, as well as mixtures of stereoisomers, as would be recognized by a skilled artisan. In some embodiments, the compounds described herein can contain one or more chiral centers. Disclosure of such compounds, unless otherwise specified, includes racemic mixtures, diastereomers, enantiomers, and mixtures containing one or more stereoisomer. Further, unless otherwise specried, the disclosed compounds encompass racemic forms of the compounds in addition to individual stereoisomers, as well as mixtures containing any of these. The word "compound," as used herein, includes any chemical structure in which two or more chemical elements are bonded together. Thus, "compound" includes, but is not limited to, small molecules, cross-linkers, monofunctional molecules, monomers, and polymers.

The term "ring atom" means an atom that is part of a cyclic ring structure. By this definition, a benzyl group has six ring atoms and tetrahydrofuran has five ring atoms. A heterocyclic ring is a ring having a heteroatom in the ring structure (i.e. one of the ring atoms is a heteroatom) as opposed to a heteroatom-substituted ring where a ring atom is bonded to a heteroatom that is not a ring atom. For example, tetrahydrofuran is a heterocyclic ring and 4-N,N-dimethylamino-phenyl is a heteroatom-substituted ring.

Starting from limonene, derivatives with one, two, or four hydroxyl groups are synthesized. Each of these precursor derivatives is functionalized with phosphorus-based, flame-retardant moieties via one or more steps. The phosphorus moiety can either possess a reactable group from monofunctional linkers, cross-linkers, or polymers, or it can possess aklyl, aryl, alkyoxy, or aryloxy groups for small molecule derivatives. This affords a broad range of possible flame-retardant molecules that are used in numerous polymer platforms, either as blended additives, reactive additives, or as polymeric materials themselves.

FIG. 1 illustrates a method 100 of forming flame-retardant compounds and materials based on limonene-derived flame-retardant small molecules, according to some embodiments. The method includes forming a limonene-based derivative at operation 105. The derivatives may have one, two, four, or more hydroxyl groups to which phosphorus-based flame-retardant molecules with functionality (such as, for example, alkenyl, allyl, epoxide, and carbonate) can be bound. In some embodiments, limonene may be reacted with itself to form a product, at which point the product can be functionalized with hydroxyl moieties via known oxidation methods. Examples of limonene derivatives are discussed in greater detail with respect to FIGS. 2A and 2B.

Method 100 includes forming a phosphorus-based flame-retardant molecule at operation 110. The phosphorus-based flame-retardant molecule has either a phosphoryl or a phosphonyl moiety (collectively referred to as an FR group) with an attached R functional group. The R groups that are attached to the FR groups can vary, as is discussed in greater detail below. The phosphorus-based flame-retardant molecules can be phosphate- or phosphonate-based flame-retardant molecules. The structures and syntheses of phosphorus-based flame-retardant molecules are discussed in greater detail with respect to FIGS. 2C and 2D. It should be noted that the formation of a limonene derivative in operation 105 is illustrated as occurring before the formation of the phosphorus-based flame-retardant molecule in operation 110. Operation 105 can occur after operation 110 or operations 105 and 110 can occur simultaneously in some embodiments.

Method 100 includes reacting the limonene-based derivative with the phosphorus-based flame-retardant molecule to form a limonene-based flame-retardant compound at operation 115. The identity of the limonene-based flame-retardant molecule is determined by the limonene derivative and the phosphorus-based flame-retardant molecule used in the reaction. The flame retardant groups are bonded to hydroxyl groups on the limonene derivatives in a reaction between the limonene derivatives and the phosphorus-based flame-retardant molecules. The syntheses and structures of limonene-based flame-retardant compounds are discussed in greater detail with respect to FIGS. 3A, 3B, 4, and 5. The limonene-based flame-retardant compounds can be monomers. Depending on the number of hydroxyl moieties and phosphorus moieties, the limonene-based flame-retardant compounds can be monomers, polymerized, bound to polymer chains, and/or serve as a cross-linker that makes a polymer flame retardant.

Method 100 includes forming a flame-retardant polymer at operation 120. The limonene-based flame-retardant compounds can be monomers, polymerized, or added to another polymer, giving a limonene-based flame-retardant polymer. The limonene-based flame-retardant compounds can be added to a polymer as small molecules, serve as cross-linkers, or bound monofunctional molecules. Further, the limonene-based flame-retardant compounds can be polymerized in a reaction with a base and/or a second monomer. Additionally, in some embodiments, the limonene-based flame-retardant compounds can be polymerized in a reaction with a Ziegler-Natta catalyst. Polymerization reactions with the limonene-based flame-retardant compounds are discussed in greater detail with respect to FIG. 6B.

Figure 2A:
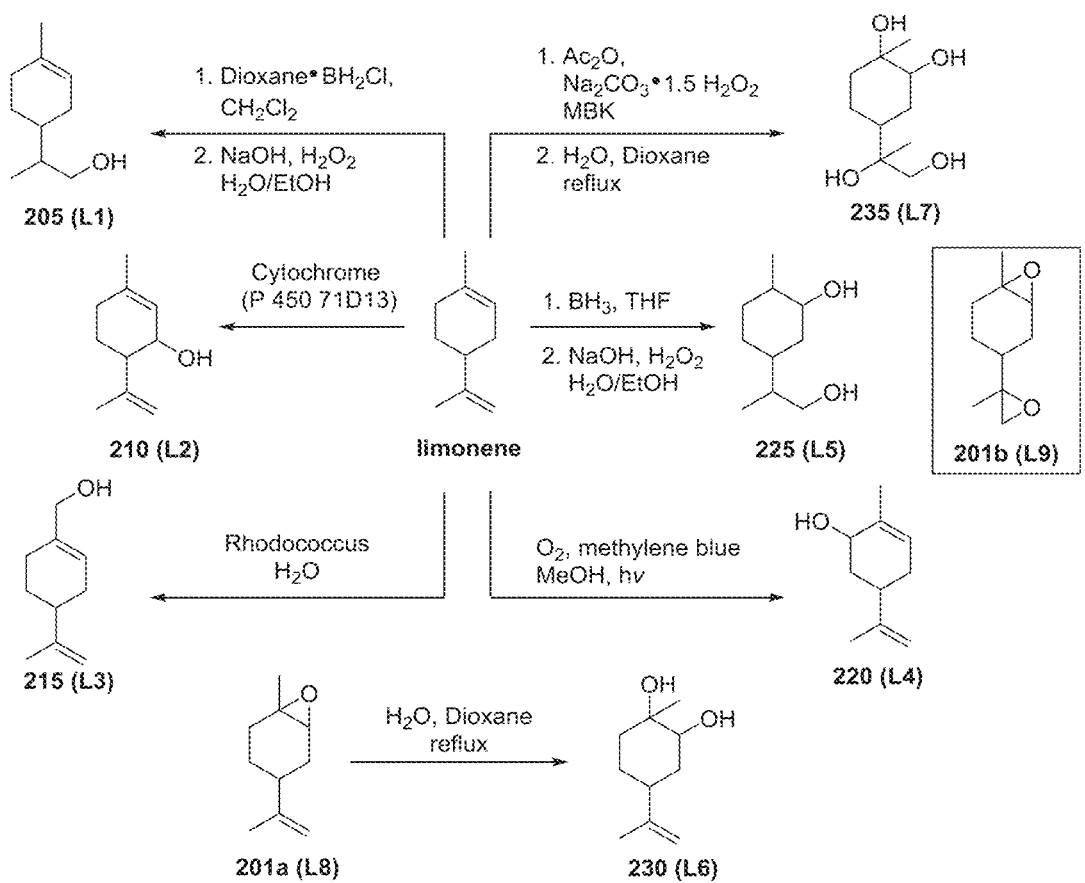
FIG. 2A shows a chemical reaction diagram illustrating conventional methods of synthesizing hydroxyl-functionalized limonene derivatives.

The synthesis of some hydroxyl-functionalized limonene derivatives is shown in FIG. 2A. All stereoisomers of limonene and all stereoisomers of the limonene-derived products can be used. These syntheses have been previously reported in the literature and result in a variety of limonene-derived molecules with one, two or four hydroxyl groups in various positions. These hydroxyl groups are then reacted with phosphorus-based molecules as described further below.

As shown in FIG. 2A, alcohol 205 (L1) is synthesized from limonene by a hydroboration-oxidation according to the following procedure. An oven-dried 50 ml round-bottom flask provided with a septum inlet and stirring bar is cooled to about 0° C. under nitrogen. The flask is charged with dioxane-$BH_2Cl$ in dichloromethane ($CH_2Cl_2$, 8.7 ml, 5 mmol). To this is added limonene (10 mmol). The contents are further stirred at about room temperature. The reaction mixture is treated with slow addition of water followed by addition of sodium hydroxide (NaOH, 7.0 mL, 3 M, 21 mmol). Ethanol (EtOH, 3.0 ml) is added followed by the slow addition of hydrogen peroxide ($H_2O_2$, 6 mmol), and the contents are further stirred at about room temperature for about 3 h and then at about 40° C. for about 1 h. The organic compound is then extracted into diethyl ether. Drying, followed by standard procedures for solvent removal and purification are then performed to give alcohol 205 (L1).

As further shown in FIG. 2A, alcohol 210 (L2) can be synthesized using cytochrome P450 according to the following procedure. A reactor (i.e., an eletro-enzymatic reactor) or fermentation vessel is charged with an aqueous buffer solution having a pH between about 5 and about 8, and oxidant such as oxygen gas or hydrogen peroxide, an enzyme, and limonene or (–)-4S-limonene. An enzyme, such as limonene-3-hydroxylase, is selected from a class of enzymes known as cyctochromes $P_{450}$. The reaction may be carried out in a bisphasic organic-aqueous mode where limonene may be added to the reaction mixture as the neat organic phase or in a mixture with other hydrocarbon or ether solvents. Variants of the enzyme that exhibit tolerance for organic solvents or limonene may be chosen from the class of enzymes known as cyctochromes $P_{450}$, and may have undergone modification of nucleic acids encoding to enhance this tolerance. The reaction may be carried out in a broad range of temperatures, typically in the range between about 5° C. and about 100° C., and preferably between 15° C. and about 60° C. The products may be recovered by extraction after the desired product concentration has been achieved or, in the case of the biphasic organic-aqueous reaction, by distillation of the organic phase which may be periodically withdrawn from the reactor. The product may be further purified by distillation, crystallization, or chromatography.

As further shown in FIG. 2A, alcohol 215 (L3) can be synthesized using a biotransformation of limonene by *Rhodococcus* sp. ALK2-E1 and *Rhodococcus* sp. HXN-1900 in water according to the following procedure. Frozen cell pellets of reactor-grown *Mycobacterium* Sp. HXN1500 and/or *Mycobacterium* Sp. HXN-1900 are suspended in a $K_2HPO_4/KH_2PO_4$-buffer (50 mM pH 7.0) to an $OD_{540}$ of 10-12. Quantities of 0.5 ml of this cell suspension are transferred to a 2.4 ml well of a square deepwell microtiter plate (Riplate, Ritter, Germany) that was detoxified and flattened. Subsequently, 4 μl limonene was added and the plate was covered with a spongy silicone plate (thickness 8 mm, non-permeable film at both sides, quality 2660 shore, Maag Technik AG, DUbendorf, Switzerland), perforated with 96 holes of 1.5 mm diameter (holes positioned exactly above the centers of the wells) and a rigid stainless steel lid (Kühner AG, Basel, Switzerland). The microtiter plate and the lid were clamped together and mounted on an orbital shaker with a shaking diameter of 5 cm using equipment from Kühner AG, (Basel, Switzerland). The microtiter plate is then subjected to 2 hours of orbital shaking at 300 rpm, 5 cm shaking amplitude, at about 25° C. The microtiter plate is then centrifuged for 15 min at 4000 rpm. Analysis by, for example, HPLC-MS (Agilent 1100 series) is then used to monitor product formation. Standard procedures for isolation and purification are then performed to provide alcohol 215 (L3), As further shown in FIG. 2A, alcohol 220 (L4) can be synthesized using a photochemical oxidation of limonene according to the following procedure. Limonene (5 mmol) and methylene blue (5 wt %) are dissolved in MeOH (10 ml). The solution is bubbled with pure oxygen gas for about 1 min with stirring. The solution was then stirred at about 5° C. for about 3 h under a white 16 W LED lamp (FAWOO-Tech. Korea, LH16-AFE39S-White). Standard procedures for quenching, solvent removal, and purification are then performed to provide alcohol 220 (L4).

As further shown in FIG. 2A, alcohol 225 (L5) can be synthesized using a hydroboration-oxidation of limonene according to the following procedure. A solution of limonene (2.5 ml, 1 M in THF) and a solution of $BH_3$-THF (2.5 ml, 1 M in THF) are combined at a T-piece (each stream runs at 2.0 ml min$^{-1}$) and reacted at about room temperature in a 2 ml PFA reactor coil until completed. The combined stream is then combined at a T-piece with an aqueous solution of NaOH (0.42 M in $H_2O_2$ (20% v/v):$H_2O$:EtOH=20:42:38) and reacted at about room temperature in a 4.2 ml PFA reactor coil. To the resulting mixture is added an aqueous saturated solution of $NH_4Cl$, the phases are separated, and the organic layer is extracted three times with $Et_2O$. The combined organic layers are washed three times with $H_2O$, washed once with brine, and dried. Standard solvent removal procedures and standard purification methods well known to those skilled in the art are then performed to give alcohol 225 (L5) as a diol.

As further shown in FIG. 2A, alcohol 230 (L6) can be synthesized in two steps an epoxidation followed by ring opening of an epoxide (limonene oxide, 201*a*(L8)) using hot water as a mild Brønsted acid catalyst. Limonene oxide 201*a* (L8) is made according to the following procedure. Limonene (125 g, 477 mmol) and $CH_2Cl_2$ (1000 ml) are added to a reaction flask, and the resulting solution is cooled with an ice bath to a temperature in the range of about 0° C. to about 10° C. Then, 70% m-chloroperbenzoic acid (m-CPBA, 1 equiv, 477 mmol) is added with stirring in small increments over a period of time of about 110 minutes, while maintaining the temperature of the reaction mixture below about 15° C. The reaction mixture is stirred for about 12 h, while maintaining the temperature below about 15° C. The precipitate is filtered off and discarded, and the organic filtrate is washed twice with 500 ml portions of 10% aqueous $Na_2SO_3$, twice with 500 ml portions of saturated aqueous $Na_2CO_3$ solution, and twice with 500 ml portions of water. The organic extracts are dried over anhydrous $MgSO_4$, and then filtered. Basic alumina (50 g) is then added to the organic filtrate, with the mixture stirred for a period of time of about 45 minutes, and then filtered. Standard procedures for solvent removal and purification are then performed to give limonene oxide 201*a* (L8).

To a 25 ml round bottom flask equipped with a condenser is added a solution of limonene oxide 201*a* (L8) (0.4 mmol) in distilled water (6 ml) and 1,4-dioxane (6 ml). The reaction mixture is heated to reflux and is monitored by thin layer chromatography (TLC). After completion, the mixture is extracted with EtOAc to give a crude product which is purified by flash column chromatography to yield alcohol 230 (L6) as a diol.

As further shown in FIG. 2A, alcohol 235 (L7) can be synthesized in 2 steps going through a diepoxide 201*b* (L9). Limonene (1.36 g, 10 mmol) is dissolved in butyl acetate (25 ml). Sodium percarbonate ($Na_2CO_3$-1.5 $H_2O_2$, 10.5 g, 66.7 mmol) and acetic anhydride ($Ac_2O$, 10.2 g, 100 mmol) is added thereto. The mixture is stirred at about 60° C. After about 12 hours, the reaction solution is washed with water to remove acetic acid and sodium acetate, which were generated as by-products and the remaining $H_2O_2$ and butyl acetate are distilled off from the organic phase by distillation. Alternately, diepoxide (not shown) can be made by the following procedure. Limonene (125 g, 477 mmol) and methylene chloride (1000 ml) are added to a reaction flask, and the resulting solution cooled with an ice bath to a temperature in the range of about 0° C. to about 10° C. Then, 70% m-chloroperbenzoic acid (m-CPBA, 1050 mmol) is added with stirring in small increments over a period of time of about 110 minutes, while maintaining the temperature of the reaction mixture below about 15° C. The reaction mixture is stirred for about 12 h, while maintaining the temperature below about 15° C. The precipitate is filtered off and discarded, and the organic filtrate is washed twice with 500 ml portions of 10% aqueous $Na_2SO_3$, twice with 500 ml portions of saturated aqueous $Na_2CO_3$ solution, and twice with 500 ml portions of water. The organic extracts are dried over anhydrous $MgSO_4$, and then filtered. Basic alumina (50 g) is then added to the organic filtrate, with the mixture stirred for a period of time of about 45 minutes, and then filtered. Standard procedures for solvent removal and purification are then performed to give limonene diepoxide (not shown). The diepoxide 201*b* (L9) may be ring-opened using the procedure shown above with modified quantities of reagents to give alcohol 237 (L7) as a tetra-hydroxyl compound.

Figure 2B:
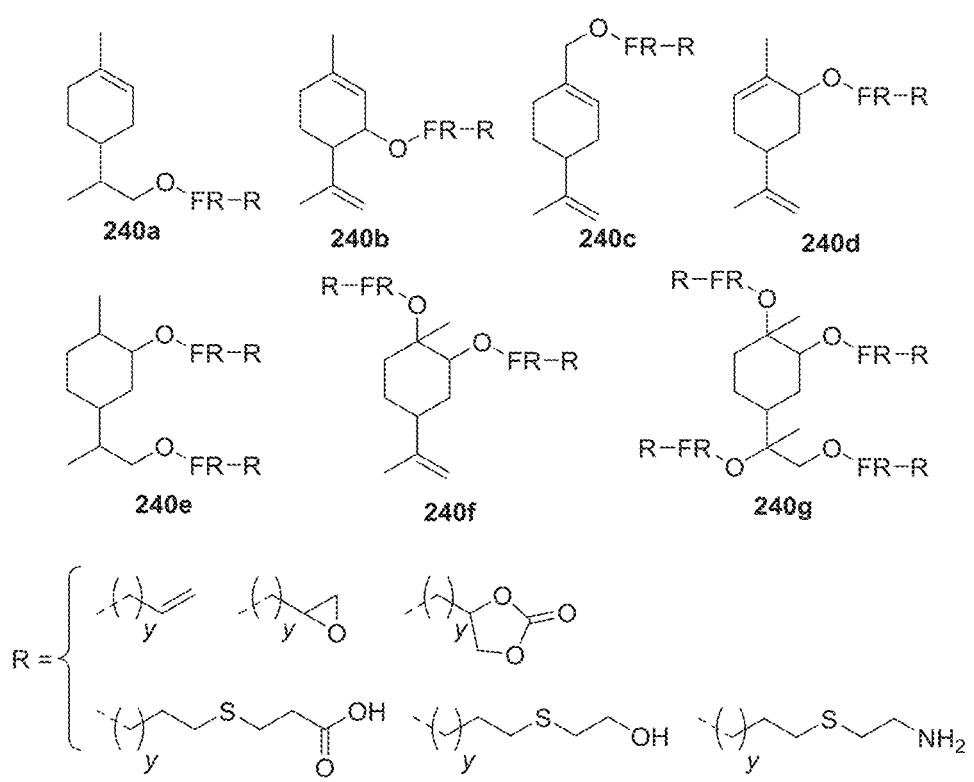
FIG. 2B shows exemplary molecular structures of R-functionalized limonene-based flame-retardant molecules according to some embodiments.
Figure 2C:
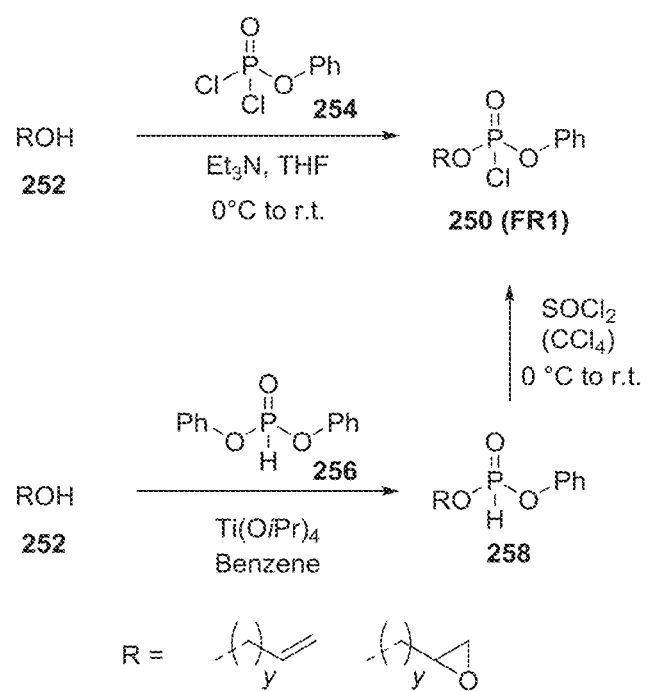
FIG. 2C shows two methods of synthesizing R-functionalized phosphate-based flame-retardant molecules according to some embodiments.
Figure 2D:
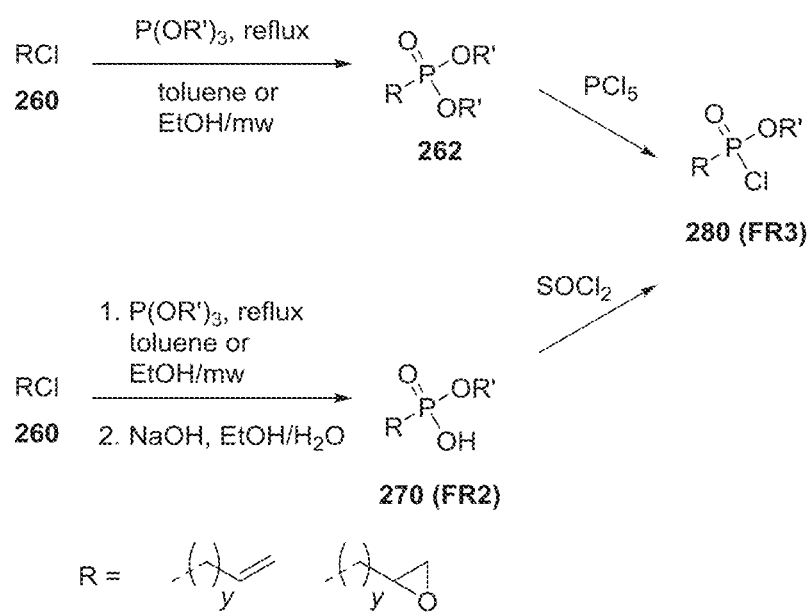
FIG. 2D shows two methods of synthesizing R-functionalized phosphonate-based flame-retardant molecules according to some embodiments.

FIG. 2B shows embodiments of limonene-based flame-retardant compounds 240*a*-240*g*. Compounds 240*a*-240*g* can be derived from the molecules shown in FIG. 2A that possess an alkene, 205 (L1)-235 (L7), by having the hydroxyl group react with either allyl functionalized 250 (FR1; FIG. 2C) or 280 (FR3; FIG. 2D), where "FR" represents a phosphate or phosphonate linkage, such that the R groups may be attached directly to the phosphorus atom or through an oxygen atom. Through their functionality, 240*a*-240*g* can be used as either cross-linkers or polymers for systems that react with, for example alkenes such as allyl and vinyl groups. While alkenyl (e.g., allyl/vinyl groups), epoxy group, and carbonate group with a single methylene spacer group (y=1) is illustrated here, alkyl chains of varying lengths (e.g., y=1-12; one to twelve methylene spacer groups) can be used. The thioether R groups may also have varying lengths, such as between about 1 to 12 methylene spacer groups. The dotted line bond indicates a connection to the phosphate group or phosphonate group of the FR group.

One skilled in the art would appreciate that the FR—R groups may be the same or different within a single limonene-based flame-retardant compound. For example, in difunctional derivative 240*e*, one FR—R group can be a phosphate with an allylic R group, while the other FR—R group can be a phosphonate with an epoxide R group.

Figure 4:
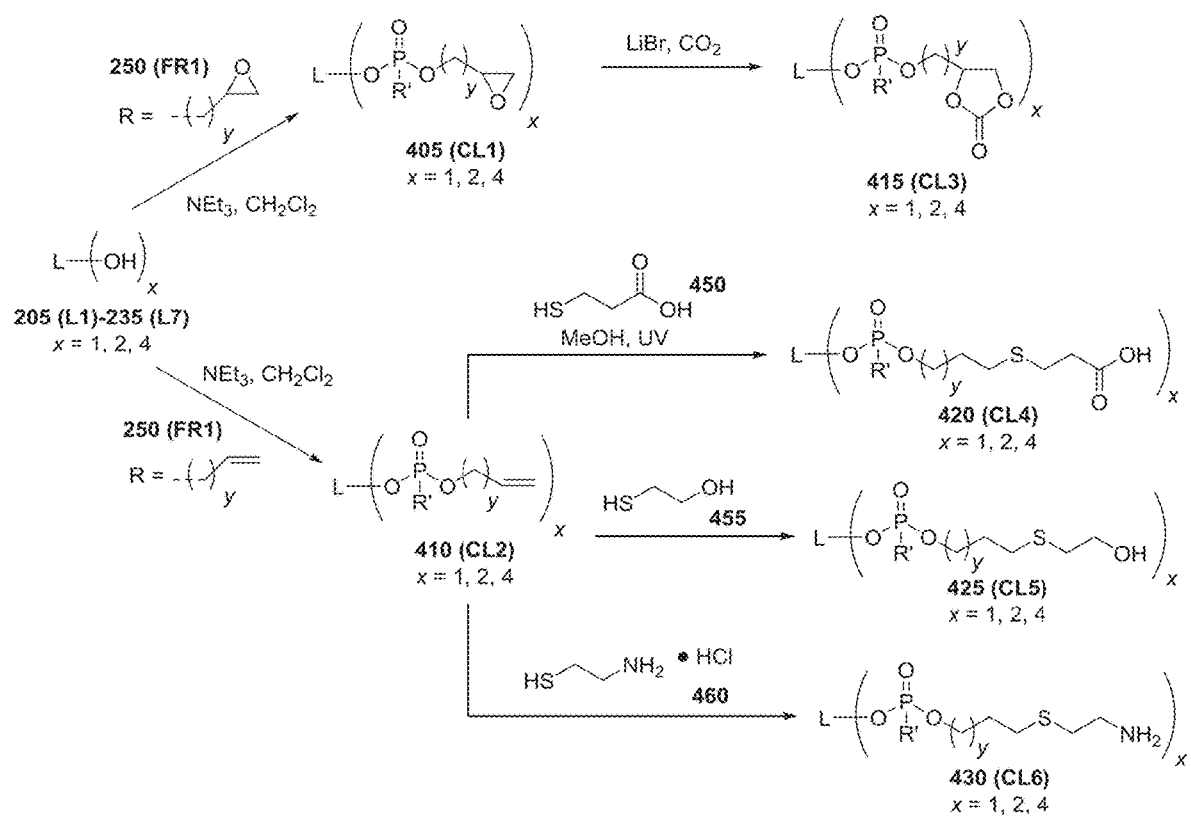
FIG. 4 shows methods of synthesizing phosphate-based, monofunctional limonene-based flame-retardant compounds and phosphate-based, limonene-based flame-retardant cross-linker compounds according to some embodiments.
Figure 5:
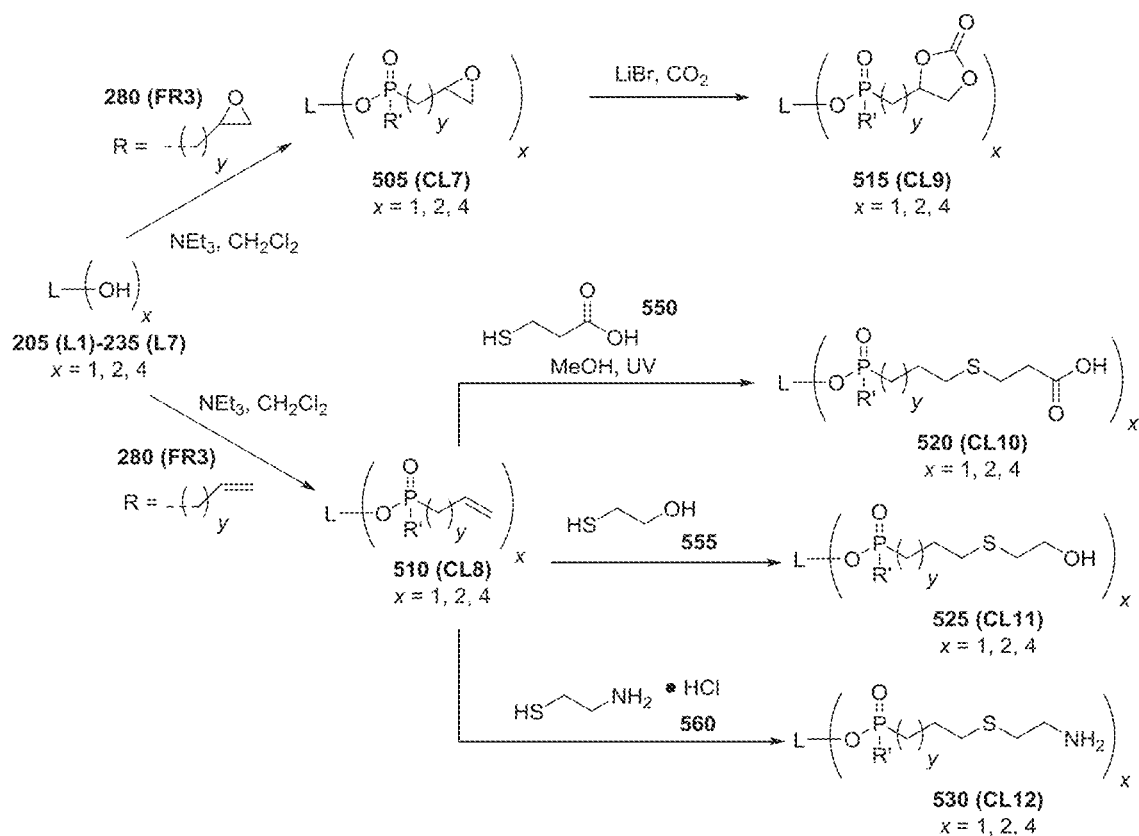
FIG. 5 shows methods of synthesizing phosphonate-based, monofunctional limonene-based flame-retardant compounds and phosphonate-based, limonene-based flame-retardant cross-linker compounds according to some embodiments.

Multi-alkene limonene derivatives, 240*a*, 240*b*, 240*c*, 240*d*, 240*f* (R=allyl group), and the limonene oxides, limonene oxide 201*a* (L8) and limonene diepoxide 201*b* (L9) can react at multiple sites. The terminal alkenes can be used as either crosslinkers or as monomers for polymerization. The dual-alkene system can then be reactive in a similar fashion as shown in FIGS. 4 and 5 via the thiol-ene chemistry. Additionally, it is possible to epoxidize both alkene systems via reaction with a reagent such as m-CPBA. These epoxides can also be converted into carbonates by procedures known to those skilled in the art. Similarly, the limonene oxide compounds can be used in reactions (cross-linking, polymerization) where epoxy groups are used.

The limonene derivatives and limonene-based flame-retardant compounds have several variable positions. These positions can have functional groups (e.g., R groups) that will participate in polymerization reactions, or bind to polymers. The positions can also have substituents (e.g., phenyl (Ph) or other alkyl groups) that do not participate in binding or polymerization. When the limonene-based flame retardant compound has no functional groups to participate in binding or polymerization, it can be blended with a polymer as a flame-retardant small molecule. When the limonene-based flame-retardant compound has a single functional group (e.g., 240*a*), it can bind to an active site in a polymer chain, or be polymerized. Additionally, such compounds can be blended with a polymer as a flame-retardant small molecule. Further, when the limonene-based flame-retardant compound has more than one functional group (e.g., 240e), it can bind to one or more active sites in a polymer chain, act as a cross-linker, or be polymerized. Additionally, such compounds can be blended with a polymer as a flame-retardant small molecule. These properties are discussed in greater detail below.

FIG. 2C is a chemical reaction diagram illustrating two methods of synthesizing an R-functionalized phosphate-based flame-retardant molecule 250 (FR1) according to some embodiments. In both methods, an alcohol 252 is a starting material for the R-functionalized phosphate-based flame-retardant molecule 250 (FR1). The alcohol 252 has either an allyl R group or an epoxy R group. While alkenyl (e.g., allyl/vinyl groups) and epoxy groups with a single methylene spacer group (y=1) is illustrated here, alkyl chains of varying lengths (e.g., y=1-12; one to twelve methylene spacer groups) can be used. Additionally, alcohols with acrylate substituents may be used in some embodiments. The dotted line bond indicates a connection to the phosphate group. In FIGS. 2C and 2D, the phenyl groups of phosphorus compounds 254 and 256 may be substituted by other aryl groups or other alkyl groups (such as ethyl, methyl, propyl, and isopropyl).

In one method, alcohol 252 is reacted with phenyl dichlorophosphate 254 in a tetrahydrofuran (THF) solution containing triethylamine ($Et_3N$). A chloride on the phenyl dichlorophosphate is replaced by the alcohol 252, forming the R-functionalized phosphate-based flame-retardant molecule 250 (FR1). This method is carried out in a temperature range of about 0° C. to about room temperature ("r.t.", e.g., about 15° C. to about 25° C.), and can be monitored by thin layer chromatography (TLC). Standard procedures of quenching, solvent removal, and purification are performed to give the R-functionalized phosphate-based flame-retardant molecule 250 (FR1).

Alternately, the alcohol 252 is reacted with diphenyl phosphite 256 and titanium isopropoxide ($Ti(OiPr)_4$) in benzene to produce a precursor 258 to the R-functionalized phosphate-based flame-retardant molecule 250 (FR1). In this reaction, the precursor 258 is formed when a phenyl (Ph) substituent on diphenyl phosphite is replaced by the R group from the alcohol 252. The precursor 258 is then reacted with thionyl chloride ($SOCl_2$) in carbon tetrachloride ($CCl_4$) over a temperature range of about 0° C. to about r.t., monitoring by TLC. Standard procedures of quenching, solvent removal, and purification are performed to give the R-functionalized phosphate-based flame-retardant molecule 250 (FR1).

FIG. 2D is a chemical reaction diagram illustrating methods of synthesizing an R-functionalized phosphonate-based flame-retardant molecule 280 (FR3) according to some embodiments. In both methods, an organochloride 260 is a starting material for the R-functionalized phosphonate-based flame-retardant molecule 280 (FR3). The organochloride has an alkenyl R group, allyl R group or an epoxy R group (such as, for example, epichlorohydrin). As in the case of the alcohol 252, other organochlorides 260 with alkyl chains of varying lengths (e.g., y=1-12, one to twelve methylene spacer groups) could be used. Additionally, organochlorides with acrylate substituents can be used in some embodiments. The dotted line bond indicates a connection to the phosphonate group.

In one method, the organochloride 260 is reacted with a phosphorus reactant ($P(OR')_3$) (such as triphenyl phosphite ($P(OPh)_3$)). R' may also be other alkyl or aryl groups, with the reactions proceedings similarly. The mixture is heated, either by refluxing in toluene or microwaving (mw) in ethanol (EtOH), and the reaction can be monitored by TLC. Standard procedures of quenching, solvent removal, and purification are performed to give a phosphonyl ester precursor 262 to the R-functionalized phosphonate-based flame-retardant molecule 280 (FR3). The phosphonyl ester precursor 262 is reacted with phosphorus pentachloride ($PCl_5$) in a nonpolar solvent such as $CCl_4$ to form the molecule 280. Standard procedures of quenching, solvent removal, and purification are performed to isolate the R-functionalized phosphonate-based flame-retardant molecule 280 (FR3).

Alternately, a mixture of the organochloride 260 and a phosphorus reactant ($P(OR')_3$) (such as triphenyl phosphite ($P(OPh)_3$)) is heated, either by refluxing in toluene or microwaving (mw) in ethanol (EtOH), forming a phenylphosphinic acid precursor 270 (FR2) to the R-functionalized phosphonate-based flame-retardant molecule 280 (FR3). The reaction is then quenched by raising the pH of the solution. In this example, an ethanol (EtOH)/water ($H_2O$) solution of sodium hydroxide (NaOH) is added to the reaction mixture. However, in some embodiments, bases other than sodium hydroxide, such as potassium hydroxide or lithium hydroxide, are used to quench the reaction. When the reaction has been quenched, thionyl chloride ($SOCl_2$) is added to the phenylphosphinic acid precursor 270 (FR2) (R'=Ph). Upon completion, the reaction mixture is cooled to room temperature, and extracted with diethyl ether. The combined aqueous layers are acidified with an aqueous acid such as 3M HCl, and extracted with diethyl ether. The solvents are removed in vacuo and the crude product may be purified by recrystallization. Subsequently, the phenylphosphinic acid product is added, dropwise, to $SOCl_2$ (excess) at 0° C. The mixture is allowed to warm up to room temperature, or heated to reflux and stirred for 2 hours. The reaction is monitored by TLC. Standard procedures of quenching, solvent removal, and purification are performed to give the R-functionalized phosphonate-based flame-retardant molecule 280 (FR3). Of note, 270 (FR2) may also be used as an R-functionalized phosphonate-based flame-retardant molecule.

Figure 3A:
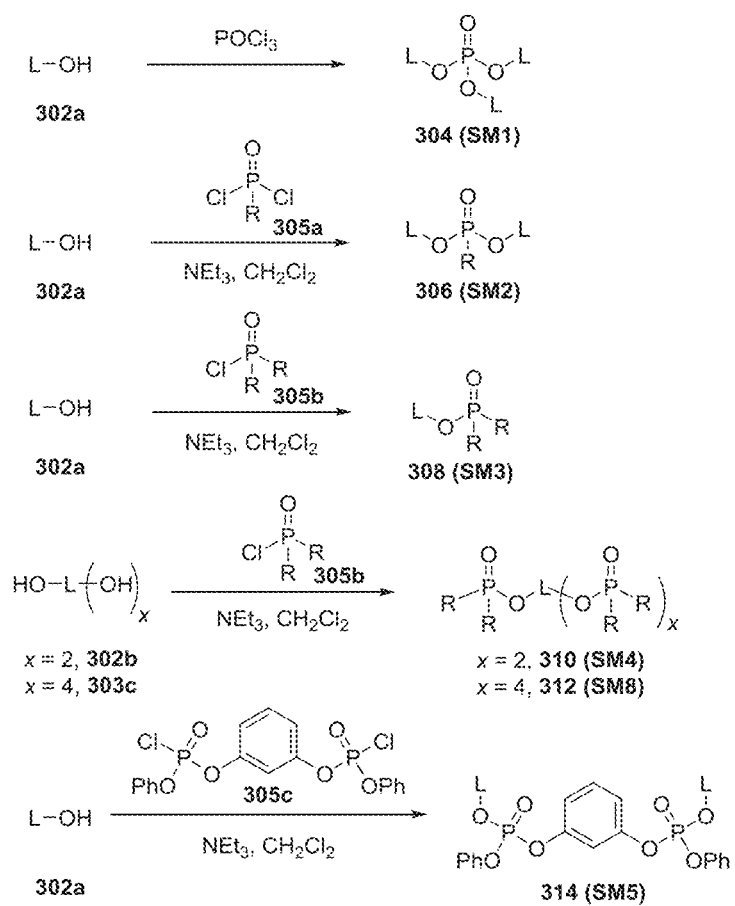
FIG. 3A shows methods of synthesizing limonene-based flame-retardant monomers according to some embodiments.
Figure 3B:
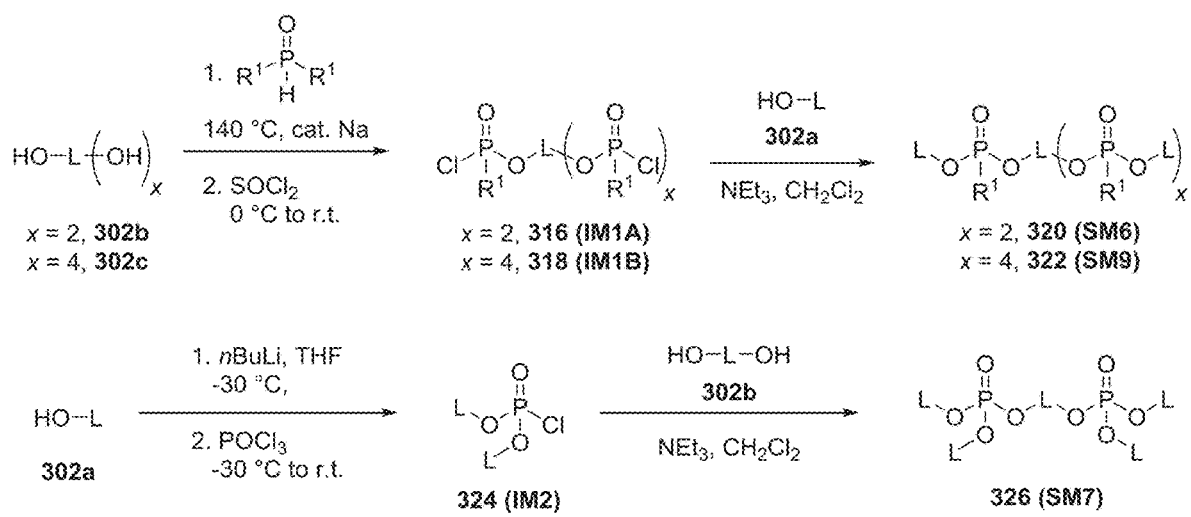
FIG. 3B shows methods of synthesizing limonene-based flame-retardant monomers according to some embodiments.

FIG. 3A and FIG. 3B show syntheses of small molecule limonene-based flame-retardant compounds from hydroxyl-functionalized limonene derivatives 302a-302c (x=1, 2, 4) according to some embodiments. Various limonene derivatives, such as those in FIG. 2A, can be reacted with different phosphorus reagents to give singly, doubly, triply or more substituted molecules, molecules with single phosphate groups, and molecules with two phosphate groups. This variability can be used to tune the renewable and phosphorus percentages. L-OH, and $HO-L(-OH)_x$ represent the mono-, di-, and tetra-hydroxyl limonene derivatives in FIG. 2A, and any and all of the hydroxides in those molecules will participate in the reactions of FIGS. 3A and 3B.

In FIGS. 3A and 3B, L is a limonene derivative as defined above, wherein each L is the same or different; R is an alkyl group, a substituted alkyl group, an aryl group, a substituted aryl group, an alkoxy group, a substituted alkoxy group, an aryloxy group, or a substituted aryloxy group, wherein each R is the same or different; and $R^1$ is an alkoxy group, a substituted alkoxy group, an aryloxy group, or a substituted aryloxy group, wherein each $R^1$ is the same or different. In some embodiments, the small molecule (SM) limonene-based flame-retardant compounds 304 (SM1), 306 (SM2), 308 (SM3), 310 (SM4), 312 (SM8), 314 (SM5), 320 (SM6), 322 (SM9), and 326 (SM7) can be blended with a polymer to impart flame retardancy to a polymer. Depending on the functionality, these compounds can be polymerized, bound to polymer chains, or serve as cross-linkers for polymers.

The phosphorus group may be a phosphate-based flame-retardant molecule or a phosphonate-based flame-retardant molecule. Herein, phosphoryl and phosphonyl moieties in the phosphate- and phosphonate-based compounds, respectively, may be replaced by the abbreviation "FR" in order to simplify illustrations of the molecular structures.

"FR" includes phosphorus groups, phosphate groups, phosphonate groups, phosphoryl groups, and phosphonyl groups.

In general, the reactions can be carried out in multiple steps to allow formation of small molecules (SM) having same or different limonene groups (L), same or different phosphorus groups (FR moieties), or combinations thereof. Because the degree of functionality can be varied (via, for example, R, R', L, and phosphorus group) allows varied small molecules. In some embodiments, varying the R and $R^1$ on the phosphorus groups result in compounds with different functionality. For example, R and $R^1$ may be unreactive alkyl (e.g., ethyl), aryl (e.g., Ph), alkoxy (e.g., OEt), aryloxy (e.g., OPh) groups. Alternately, R and $R^1$ can include functionality such as vinyl groups and epoxide groups, allowing for further chemical manipulation.

The reactions in FIGS. 3A and 3B are not limited by any properties of the R groups of the phosphorus reagent, that is, the sterics, electrostatics, tertiary geometries do not hinder any potential reactions.

As shown in FIG. 3A, small molecule ester 304 (SM1) is formed by mixing monohydroxyl-functionalized limonene (L-OH) 302a with $POCl_3$ (phosphoryl chloride). This reaction can be done in one or more steps such that different limonene derivatives 302a may be used. Phosphoryl chloride (50 mmol) and alcohol L-OH (200 mmol) are added under argon successively to a round bottom flask containing 120 ml of toluene. The mixture is refluxed for about 8 to about 10 h under magnetic stirring. The solution is concentrated with a rotary evaporator and the viscous residue was co-evaporated twice with 100 ml of toluene. Standard procedures for purification are then performed to give phosphate 304 (SM1).

In some embodiments, L can be one or more different hydroxyl-functionalized limonene compounds. For example, compound 304 (SM1) can have three different hydroxyl-functionalized limonene groups attached to the phosphorus group.

Small molecules 306 (SM2), 308 (SM3), 310 (SM4), 312 (SM8), and 314 (SM5) are formed by mixing various hydroxyl-functionalized limonene (L-OH) 302a-302c (x=1, 2, 4) with various phosphorus reactants (305a-305c), and stoichiometric amounts of organic amine (e.g., trimethylamine, $Et_3N$) in dichloromethane ($CH_2Cl_2$). Hydroxyl groups (—OH) are an integer x of 1, 2, or 4. Limonene derivative 302a may include molecules such as alcohols 205 (L1)-220 (L4). Limonene derivative 302b may include molecules such as diols 225 (L5) and 230 (L6). Limonene derivative 302c may include molecules such as tetrahydroxyl 235 (L7).

FIG. 3B shows the synthesis of small molecule limonene-based flame-retardant compounds from hydroxyl-functionalized limonene derivatives according to some embodiments. Small molecule limonene-based flame-retardant compounds 320 (SM6) and 322 (SM9) may be synthesized in three steps from limonene-based diol 302b and limonene-based tetra-hydroxyl 302c, respectively, by the following prophetic process. Limonene-based diol 302b (300 mmol) and phosphite 315 (900 mmol) are placed into a flask at r.t. and are purged with nitrogen for about 10 min. As a catalyst, approximately 10-15 mmol of sodium metal is added to the reaction mixture, which is heated to about 140° C. so the alcohol (R') set free is removed by distillation to give a crude monomer (not shown). The crude monomer is then reacted with thionyl chloride ($SOCl_2$) in carbon tetrachloride ($CCl_4$) over a range of about 0° C. to about r.t., and monitored for completion by TLC. Standard procedures for quenching, solvent removal and purification are then performed to produce difunctionalized limonene intermediate compound 316 (IM1A). Tetrafunctionalized limonene intermediate compound 318 (IM1B) may be synthesized in a similar manner as 316 (IM1A).

Difunctionalized-limonene intermediate compound 316 (IM1A) is then mixed with hydroxyl-functionalized limonene (L-OH) 302a and stoichiometric amounts of organic amine (e.g., trimethylamine, $Et_3N$) in dichloromethane ($CH_2Cl_2$), and stirred until completion as monitored by TLC. Standard procedures for quenching, solvent removal, and purification to produce small molecule limonene-based flame-retardant compound 320 (SM6). Small molecule limonene-based flame-retardant compound 322 (SM9) may be synthesized in a similar manner as 320 (SM6).

Small molecule limonene-based flame-retardant compound 326 (SM7) may be synthesized in three steps from hydroxyl-functionalized limonene (L-OH) 302a by the following prophetic process. Hydroxyl-functionalized limonene 302a (2 equiv.) is dissolved in tetrahydrofuran (THF, 10 ml) and diethyl ether ($Et_2O$, 10 ml) and the mixture is cooled to −30° C. Butyllithium (BuLi, 2 equiv.) is added dropwise to the solution. The mixture is stirred for about another 10 min. at −30° C., at which point phosphoryl chloride ($POCl_3$, 1 equiv.) was slowly added. The mixture is allowed to warm to ambient temperature and stirred overnight. Volatiles are removed under reduced pressure, and the resulting residue is suspended in $Et_2O$ and filtered through Celite with $Et_2O$. Standard procedures for solvent removal and purification provides chloride 324 (IM2). Chloride 324 (IM2) is then mixed with hydroxyl-functionalized limonene 302b and stoichiometric amounts of organic amine (e.g., trimethylamine, $Et_3N$) in dichloromethane ($CH_2Cl_2$). Once the reaction is complete as monitored by TLC, standard procedures for quenching, solvent removal, and purification are then performed to give small molecule limonene-based FR 326 (SM7).

FIGS. 4 and 5 detail the synthesis of linkable monofunctional flame retardants as well as limonene-derived flame-retardant cross-linkers according to some embodiments. Specifically, FIG. 4 shows the synthesis of phosphate-based, monofunctionalized and cross-linker limonene-derived, flame-retardant monomers according to some embodiments. FIG. 5 shows the synthesis of phosphonate-based, monofunctionalized and cross-linker limonene-derived, flame-retardant monomers according to some embodiments. While alkenyl (e.g., allyl/vinyl groups), epoxy group, and carbonate group with a single methylene spacer group (y=1) is illustrated in FIGS. 4 and 5, alkyl chains of varying lengths (e.g., y=1-12; one to twelve methylene spacer groups) can be used. The thioether groups may also have varying lengths, such as between about 1 to 12 methylene spacer groups. The reactions in FIGS. 4 and 5 are not limited by any properties of the R groups of the phosphorus reagent, that is, the sterics, electrostatics, tertiary geometries do not hinder any potential reaction.

In regards to FIGS. 4 and 5, one skilled in the art would appreciate that FR—R groups may be the same or different within a limonene-based flame-retardant compound. For example, in difunctional derivative 225 (L5), one hydroxyl may be converted to a phosphonate having an alkenyl group while the other hydroxyl can be converted to a phosphate having a carbonate group. This can be done by stoichiometric control when adding the 250 (FR1)/280 (FR3). Such combinations of phosphate/phosphonate, alkenyl/thioether/carbonate/epoxide allow the flame retardancy of the compounds to be tuned depending on application.

In some embodiments, when the limonene derivative 405 (CL1)-430 (CL6) has only one hydroxyl group (x=1; monofunctionalized), it can be blended with a polymer, polymerized, and/or bound, i.e. chemically, to polymer chains to impart flame retardancy. When the limonene derivative 405 (CL1)-430 (CL6) has two or more hydroxyl groups (e.g., x=2, 4), it can be blended with a polymer, polymerized, bound to polymer chains, or serve as a cross-linker for polymers to impart flame retardancy.

Phosphate-based, monofunctionalized and cross-linker limonene-derived, flame-retardant monomers 405 (CL1) are produced by reacting a hydroxyl-functionalized limonene derivative 205 (L1)-235 (L7) ((L-OH)$_x$) with epoxy-functionalized phosphate 802 (FR1). Phosphate-based, monofunctionalized and cross-linker limonene-derived, flame-retardant monomer 410 (CL2) is produced by reacting a hydroxyl-functionalized limonene derivative 205 (L1)-235 (L7) ((L-OH)$_x$) with allyl- or vinyl-functionalized phosphate 802 (FR1). In both reactions, the alcohol is reacted with a phosphorus-based flame-retardant molecule and a stoichiometric amount of an organic amine (e.g., triethylamine) in a dichloromethane ($CH_2Cl_2$) solution. Note that epoxy 405 (CL1) can be produced by reacting alkenyl (allyl- or vinyl-) functionalized 410 (CL2) with a peroxide reagent, such as meta-chloroperoxybenzoic acid (m-CPBA), in $CH_2Cl_2$, followed by standard procedures for quenching, solvent removal, and purification. Further, epoxy R groups 405 (CL1) can ring open in reactions involving nucleophiles, not just that shown in FIG. 4.

Epoxide 405 (CL1) can be a monofunctionalized limonene-based flame-retardant monomer or a cross-linker limonene-based flame-retardant monomer. Monofunctionalized and/or cross-linker, flame-retardant monomer 405 (CL1) can be blended with a polymer, polymerized, bound to polymer chains, or serve as a cross-linker for polymers to impart flame retardancy. Alkene 410 (CL2) can be a monofunctionalized limonene-based flame-retardant monomer or a cross-linker limonene-based flame-retardant monomer. Monofunctionalized and/or cross-linker, flame-retardant monomer 410 (CL2) can be blended with a polymer, polymerized, bound to polymer chains, or serve as a cross-linker for polymers to impart flame retardancy.

Phosphate-based, monofunctionalized and cross-linker limonene-derived, flame-retardant monomer 415 (CL3) may be produced by the following process. Epoxide monomer 405 (CL1) (1.0 equiv) is combined with lithium bromide (LiBr, 0.05 equiv) in acetone (35 ml) and placed into an autoclave. The atmosphere is replaced with carbon dioxide ($CO_2$, P=12 bar), and the solution is heated at about 80° C. with continuous stirring for about 12 hours. The solvent is distilled under vacuum (P=0.01 bar) at about 60° C. Deionized water is added and the aqueous phase is extracted with ethyl acetate. The organic phase is washed with brine, dried on anhydrous $Na_2SO_4$ and ethyl acetate is removed using a rotary evaporator. Standard procedures for purification are then yielding monofunctionalized and/or cross-linker, flame-retardant monomer 415 (CL3) as a carbonate. Carbonate 415 (CL3) can be a monofunctionalized limonene-based flame-retardant monomer or a cross-linker limonene-based flame-retardant monomer. Monofunctionalized and/or cross-linker, flame-retardant monomer 415 (CL3) can be blended with a polymer, polymerized, bound to polymer chains, or serve as a cross-linker for polymers to impart flame retardancy.

The following procedure may also be used to form carbonate 415 (CL3). Epoxide monomer 405 (CL1) (1.0 equiv.), Bis(triphenylphosphoranylidene) ammonium chloride (PPNCl, 10 mol %) and methyl ethyl ketone are mixed in a Teflon vessel equipped with a magnetic stirring bar, placed in a stainless steel reactor, purged three times with about 5 bar of $CO_2$, and pressurized with about 20 bar of $CO_2$ at about room temperature. The mixture is heated to about 73° C., measured inside the reactor, and stirred for about 48 h. After cooling in an ice bath, the reactor is slowly depressurized. The liquid phase is transferred into a flask and the Teflon insert is rinsed with dichloromethane. Removal of the volatiles in vacuo is followed by addition of dichloromethane until the solid dissolves completely. Drop-wise addition of MeOH may cause formation of a precipitate. If necessary, the treatment was repeated to remove remaining PPNCl from the polymer. Separation and purification can be performed by techniques known to those skilled in art to provide monofunctionalized and/or cross-linker, flame-retardant monomer 415 (CL3) as a carbonate.

Phosphate-based, monofunctionalized and cross-linker limonene-derived, flame-retardant monomers 420 (CL4), 425 (CL5), and 430 (CL6) may be produced by thiol-ene click reactions. Thiols such as 3-mercaptopropionate 450, mercaptoethanol 455, and cysteamine hydrochloride 460 may be used in the thiol-ene reaction. The reaction provides functionalized thioether groups and can be carried out with any allyl- and vinyl-functionalized compounds disclosed herein. The reaction provides different degrees of functionalization for the phosphate-based, monofunctionalized and cross-linker limonene-derived, flame-retardant monomers.

Thioether 420 (CL4) may be prepared by the following process. To a solution of alkene 410 (CL2) in a suitable solvent, such as methanol (MeOH), are added 3-mercaptopropionate 450 (6 equiv.), an amine base, and an initiator. The amine base can be a trialkyl amine such as triethylamine, or an aromatic amine such as DBU (1,8-diazobicyclo [5.4.0]undec-7-ene) and DMAP (4-dimethylaminopyridine). The thiol-ene click reaction may proceed using ultraviolet (UV) light (wavelength range from about 365 nm to about 405 nm). Suitable photoinitiators include (2,4,6-trimethylbenzoyl)diphenylphosphine oxide (TMDPO), 2,2-dimethoxy-2-phenyl acetophenone (DMPA), benzophenone, thioxanthone, and camphorquinone. The photoinduced reactions can be run at temperatures of about room temperature. Standard procedures for solvent removal and purification can then be used to provide thioether 420 (CL4). Thioether 420 (CL4) can be a monofunctionalized limonene-based flame-retardant monomer or a cross-linker limonene-based flame-retardant monomer. Monofunctionalized and/or cross-linker, flame-retardant monomer 420 (CL4) can be blended with a polymer, polymerized, bound to polymer chains, or serve as a cross-linker for polymers to impart flame retardancy.

Thioether 425 (CL5) may be prepared by the following process. To alkene 410 (CL2) is added a mercaptoethanol 455 (6 equiv.), an amine base such as those given above, and an initiator such as those given above. The photoinduced reaction can be run at temperatures of about room temperature. The reaction may be run neat or in an amount of methanol to dissolve the reaction components. Standard procedures for solvent removal and purification than then be used to provide thioether 425 (CL5). Thioether 425 (CL5) can be a monofunctionalized limonene-based flame-retardant monomer or a cross-linker limonene-based flame-retardant monomer. Monofunctionalized and/or cross-linker, flame-retardant monomer 425 (CL5) can be blended with a polymer, polymerized, bound to polymer chains, or serve as a cross-linker for polymers to impart flame retardancy.

Thioether 430 (CL6) may be prepared by the following process. To a solution of alkene 410 (CL2) in a suitable solvent, such as a pH 9 methanol (MeOH) solution, are added cysteamine hydrochloride (HCl) 460 (6 equiv.), an amine base such as those given above, and an initiator such as those given above. The photoinduced reaction can be run at temperatures of about room temperature. Standard procedures for solvent removal and purification than then be used to provide thioether 430 (CL6). Thioether 430 (CL6) can be a monofunctionalized limonene-based flame-retardant monomer or a cross-linker limonene-based flame-retardant monomer. Monofunctionalized and/or cross-linker, flame-retardant monomer 430 (CL6) can be blended with a polymer, polymerized, bound to polymer chains, or serve as a cross-linker for polymers to impart flame retardancy.

FIG. 5 shows the synthesis of phosphonate-based, monofunctionalized and cross-linker limonene-derived, flame-retardant monomers according to some embodiments. When the limonene derivative 505 (CL7)-530 (CL12) has only one hydroxyl group (x=1; monofunctionalized), it can be blended with a polymer, polymerized, and/or bound to polymer chains to impart flame retardancy. When the limonene derivative 505 (CL7)-530 (CL12) has two or more hydroxyl groups, it can be blended with a polymer, polymerized, bound to polymer chains, or serve as a cross-linker for polymers to impart flame retardancy.

Phosphonate-based, monofunctionalized and cross-linker limonene-derived, flame-retardant monomer 505 (CL7) is produced by reacting a hydroxyl-functionalized limonene derivative 205 (L1)-235 (L7) ((L-OH)$_x$) with epoxy-functionalized FR 280 (FR3). Phosphonate-based, monofunctionalized and cross-linker limonene-derived, flame-retardant monomer 510 (CL8) is produced by reacting a hydroxyl-functionalized limonene derivative 205 (L1)-235 (L7) ((L-OH)$_x$) with allyl- or vinyl-functionalized FR 280 (FR3). In both reactions, the alcohol is reacted with a phosphorus-based flame-retardant molecule and a stoichiometric amount of an organic amine (e.g., triethylamine) in a dichloromethane ($CH_2Cl_2$) solution. Standard procedures for quenching the reaction, solvent removal, and purification are then performed. Note that epoxy 505 (CL7) can be produced by reacting alkenyl (allyl- or vinyl-) functionalized 510 (CL8) with a peroxide reagent, such as meta-chloroperoxybenzoic acid (m-CPBA), in $CH_2Cl_2$, followed by standard procedures for quenching, solvent removal, and purification. Further, epoxy R groups 505 (CL7) can ring open in reactions involving nucleophiles, not just that shown in FIG. 5.

Epoxide 505 (CL7) can be a monofunctionalized limonene-based flame-retardant monomer or a cross-linker limonene-based flame-retardant monomer. Monofunctionalized and/or cross-linker, flame-retardant monomer 505 (CL7) can be blended with a polymer, polymerized, bound to polymer chains, or serve as a cross-linker for polymers to impart flame retardancy. Alkene 510 (CL8) can be a monofunctionalized limonene-based flame-retardant monomer or a cross-linker limonene-based flame-retardant monomer. Monofunctionalized and/or cross-linker, flame-retardant monomer 510 (CL8) can be blended with a polymer, polymerized, bound to polymer chains, or serve as a cross-linker for polymers to impart flame retardancy.

Phosphonate-based, monofunctionalized and cross-linker limonene-derived, flame-retardant monomer 515 (CL9) may be produced by the following process. Epoxide monomer 505 (CL7) (1.0 equiv) is combined with lithium bromide (LiBr, 0.05 equiv) in acetone (35 ml) and placed into an autoclave. The atmosphere is replaced with carbon dioxide ($CO_2$, P=12 bar), and the solution is heated at about 80° C. with continuous stirring for about 12 hours. The solvent is distilled under vacuum (P=0.01 bar) at about 60° C.

Deionized water is added and the aqueous phase is extracted with ethyl acetate. The organic phase is washed with brine, dried on anhydrous $Na_2SO_4$ and ethyl acetate is removed using a rotary evaporator. Standard procedures for purification are then yielding monofunctionalized and/or cross-linker, flame-retardant monomer 515 (CL9) as a carbonate. Carbonate 515 (CL9) can be a monofunctionalized limonene-based flame-retardant monomer or a cross-linker limonene-based flame-retardant monomer. Monofunctionalized and/or cross-linker, flame-retardant monomer 515 (CL9) can be blended with a polymer, polymerized, bound to polymer chains, or serve as a cross-linker for polymers to impart flame retardancy.

The following procedure may also be used to form carbonate 515 (CL3). Epoxide monomer 505 (CL3) (1.0 equiv.), Bis(triphenylphosphoranylidene) ammonium chloride (PPNCl, 10 mol %) and methyl ethyl ketone are mixed in a Teflon vessel equipped with a magnetic stirring bar, placed in a stainless steel reactor, purged three times with about 5 bar of $CO_2$, and pressurized with about 20 bar of $CO_2$ at about room temperature. The mixture is heated to about 73° C., measured inside the reactor, and stirred for about 48 h. After cooling in an ice bath, the reactor is slowly depressurized. The liquid phase is transferred into a flask and the Teflon insert is rinsed with dichloromethane. Removal of the volatiles in vacuo is followed by addition of dichloromethane until the solid dissolves completely. Dropwise addition of MeOH may cause formation of a precipitate. If necessary, the treatment was repeated to remove remaining PPNCl from the polymer. Separation and purification can be performed by techniques known to those skilled in art to provide monofunctionalized and/or cross-linker, flame-retardant monomer 515 (CL9) as a carbonate.

Phosphonate-based, monofunctionalized and cross-linker limonene-derived, flame-retardant monomers 520 (CL10), 525 (CL11), and 530 (CL12) may be produced by thiol-ene click reactions. Thiols such as 3-mercaptopropionate 550, mercaptoethanol 555, and cysteamine hydrochloride 560 may be used in the thiol-ene reaction. The reaction provides functionalized thioether groups, and the reaction can be carried out with any allyl- and vinyl-functionalized compounds disclosed herein. The reaction provides different degrees of functionalization for the phosphonate-based, monofunctionalized and cross-linker limonene-derived, flame-retardant monomers.

Thioether 520 (CL10) may be prepared by the following process. To a solution of alkene 510 (CL7) in a suitable solvent, such as methanol (MeOH), are added 3-mercaptopropionate 550 (6 equiv.), an amine base, and an initiator. The amine base can be a trialkyl amine such as triethylamine, or an aromatic amine such as DBU (1,8-diazobicyclo [5.4.0]undec-7-ene) and DMAP (4-dimethylaminopyridine). The thiol-ene click reaction may proceed using ultraviolet (UV) light (wavelength range from about 365 nm to about 405 nm). Suitable photoinitiators include (2,4,6-trimethylbenzoyl)diphenylphosphine oxide (TMDPO), 2,2-dimethoxy-2-phenyl acetophenone (DMPA), benzophenone, thioxanthone, and camphorquinone. The photoinduced reactions can be run at temperatures of about room temperature. Standard procedures for solvent removal and purification than then be used to provide thioether 520 (CL10). Thioether 520 (CL10) can be a monofunctionalized limonene-based flame-retardant monomer or a cross-linker limonene-based flame-retardant monomer. Monofunctionalized and/or cross-linker, flame-retardant monomer 520 (CL10) can be blended with a polymer, polymerized, bound to polymer chains, or serve as a cross-linker for polymers to impart flame retardancy.

Thioether 525 (CL11) may be prepared by the following process. To alkene 510 (CL8) is added a mercaptoethanol 555 (6 equiv.), an amine base such as those give above, and an initiator such as those given above. The photoinduced reaction can be run at temperatures of about room temperature. The reaction may be run neat or in an amount of methanol to dissolve the reaction components. Standard procedures for solvent removal and purification than then be used to provide thioether 525 (CL11). Thioether 525 (CL11) can be a monofunctionalized limonene-based flame-retardant monomer or a cross-linker limonene-based flame-retardant monomer. Monofunctionalized and/or cross-linker, flame-retardant monomer 525 (CL11) can be blended with a polymer, polymerized, bound to polymer chains, or serve as a cross-linker for polymers to impart flame retardancy.

Thioether 530 (CL12) may be prepared by the following process. To a solution of alkene 510 (CL8) in a suitable solvent, such as a pH 9 methanol (MeOH) solution, are added cysteamine hydrochloride (HCl) 560 (6 equiv.), an amine base such as those given above, and an initiator such as those given above. The photoinduced reaction can be run at temperatures of about room temperature. Standard procedures for solvent removal and purification than then be used to provide thioether 530 (CL12). Thioether 530 (CL12) can be a monofunctionalized limonene-based flame-retardant monomer or a cross-linker limonene-based flame-retardant monomer. Monofunctionalized and/or cross-linker, flame-retardant monomer 530 (CL12) can be blended with a polymer, polymerized, bound to polymer chains, or serve as a cross-linker for polymers to impart flame retardancy.

The methods of forming the limonene-based flame-retardant compounds illustrated herein can be carried out with different combinations of phosphorus-based flame-retardant molecules 250 (FR1) and 280 (FR3). In some embodiments, these processes can be carried out with either all phosphate-based flame-retardant molecules (one or more of 250 (FR1)) or all phosphonate-based flame-retardant molecules (one or more of 280 (FR3)). In other embodiments, a mixture of both phosphate- and phosphonate-based flame-retardant molecules can be used. Carrying out these processes with a mixture of phosphate- and phosphonate-based compounds (250 (FR1) and/or 280 (FR3)) can result in the production of flame-retardant limonene-based monomers with both phosphoryl and phosphonyl FR groups.

However, in some instances, adding a mixture of phosphate- and phosphonate-based compounds (250 (FR1) and/or 280 (FR3)) can result in the production of limonene-based flame-retardant monomers with all phosphoryl or all phosphonyl FR moieties. Additionally, adding a mixture of phosphate- and phosphonate-based compounds (250 (FR1) and/or 280 (FR3)) to the reaction can yield a mixture of products that includes some combination of limonene-based flame-retardant monomers with either all phosphoryl or all phosphonyl FR groups and limonene-based flame-retardant monomers with both phosphoryl and phosphonyl FR groups.

Figure 6A:
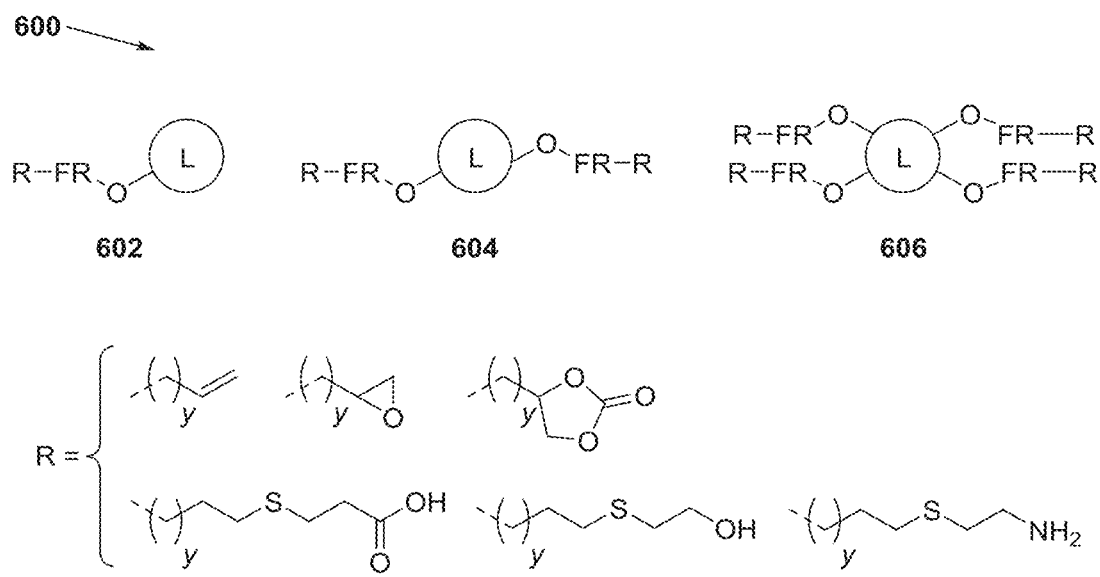
FIG. 6A shows structures of generic R-functionalized limonene-based flame-retardant monomers according to some embodiments.

FIG. 6A is a diagrammatic representation of the structures 600 of generic R-functionalized limonene-based flame-retardant monomers 602, 604, and 606, according to some embodiments. The monomers may be monofunctionalized limonene-based flame-retardant compounds 602, difunctionalized limonene-based flame-retardant compounds 604, and tetra-functionalized limonene-based flame-retardant compounds 606. Examples of compounds represented by these structures 600 are discussed in greater detail with respect to FIGS. 4 and 5. The R-functionalized limonene-based compounds 600 can be polymerized to form flame-retardant limonene-based polymers. An oval labeled "L" represents the limonene-derivative core of each monomer. Each structure shows only the ligands with R-functional groups (e.g., alkenyl (e.g., vinyl, allyl) epoxy, carbonate, and thioethers). While alkenyl (e.g., allyl/vinyl groups), epoxy group, and carbonate group with a single methylene spacer group (y=1) is illustrated here, alkyl chains of varying lengths (e.g., y=1-12; one to twelve methylene spacer groups) can be used. The thioether groups may also have varying lengths, such as between about 1 to 12 methylene spacer groups. The dotted line bond indicates a connection to the phosphate group or phosphonate group of the FR group.

In regards to FIG. 6A, one skilled in the art would appreciate that FR—R groups may be the same or different within a limonene-based flame-retardant compound. For example, in difunctional derivative 604, one hydroxyl may be linked to a phosphonate having an alkenyl group while the other hydroxyl may be linked to a phosphate having a carbonate group. This can be done by stoichiometric control when adding 250 (FR1)/280 (FR3). Such combinations of phosphate/phosphonate, alkenyl/thioether/carbonate/epoxide allow the flame retardancy of the compounds to be tuned depending on application.

Figure 6B:
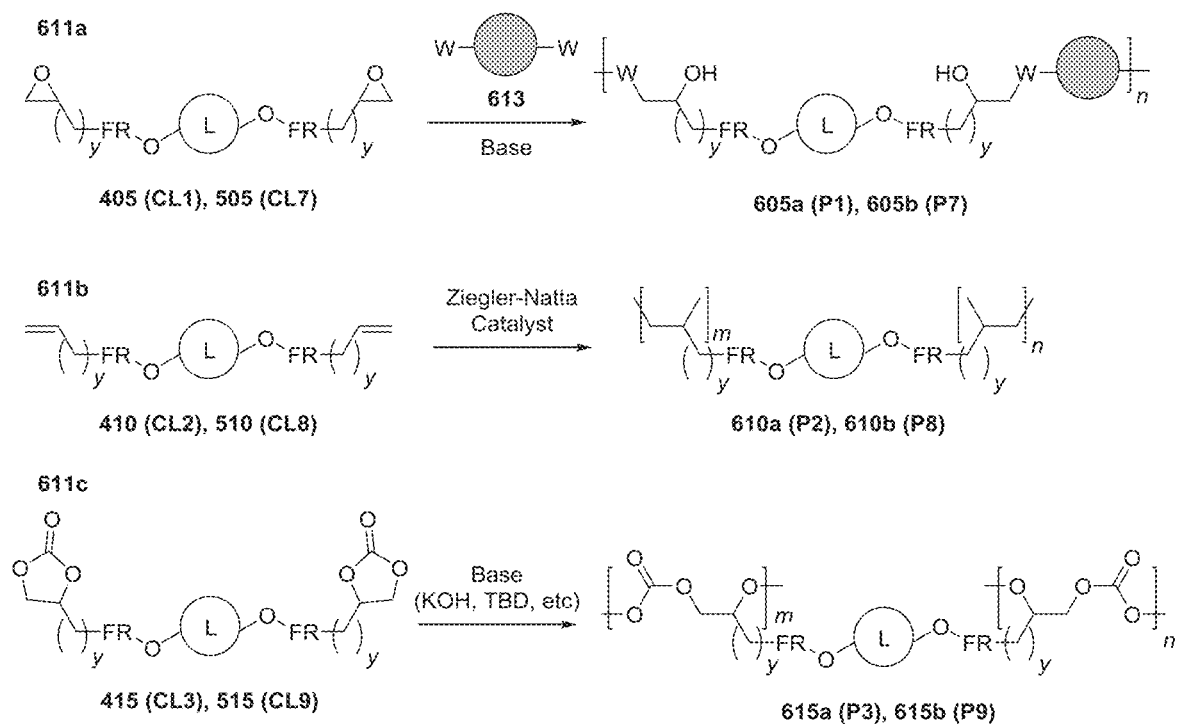
FIG. 6B shows methods of synthesizing limonene-based flame-retardant polymers from limonene-based flame-retardant monomers according to some embodiments.

FIG. 6B shows polymers derived from limonene derivatives according to some embodiments. The functionalized limonene derivatives from FIGS. 4 and 5 can be reacted with different phosphorus reagents to give polymers with one, two, or four linkages/formed bonds. The tetra-functionalized polymer is not shown, but its structure can be inferred. The reactions in FIG. 6B are not limited by any properties of the groups on the phosphorus, that is, the sterics, electrostatics, tertiary geometries do not hinder any potential reaction.

In regards to FIG. 6B, and as mentioned above, one skilled in the art would appreciate that FR—R groups may be the same or different within a limonene-based flame-retardant compound. For example, in difunctional derivative 405 (CL1), one hydroxyl may have a phosphonate having an alkenyl group while the other hydroxyl bears a phosphate having an epoxide group. This can be done by stoichiometric control when adding 250 (FR1)/280 (FR3). Such combinations of phosphate/phosphonate, alkenyl/thioether/carbonate/epoxide allow the flame retardancy of the compounds to be tuned depending on application.

The reactions 611a, 611b, and 611c of FIG. 6B illustrate the polymerization of difunctionalized limonene-based flame-retardant monomers 604 only. However, it should be noted that each of these polymerization reactions can also be carried out with the tetra-functionalized limonene-based flame-retardant monomers 606. Additionally, processes 611a and 611b can be carried out with the monofunctionalized limonene-based flame-retardant monomers 602. Further, and in some embodiments, the polymerization reactions are carried out with a combination of both difunctionalized limonene-based flame-retardant monomers 604 and tetra-functionalized limonene-based flame-retardant monomers 606, both difunctionalized limonene-based flame-retardant monomers 604 and monofunctionalized limonene-based flame-retardant monomers 602, both tetra-functionalized limonene-based flame-retardant monomers 604 and monofunctionalized limonene-based flame-retardant monomers 602, or a combination of monomers that includes tetra-, di-, and monofunctionalized monomers in any ratio.

In method 611a, epoxy-derived limonene-based flame-retardant polymers 605a (P1) and 605b (P7) are formed from difunctionalized limonene-based flame-retardant monomers 405 (CL1) and 505 (CL7) having epoxy R groups, respectively. As an example, the difunctionalized limonene-based flame-retardant compound 405 (CL1) is reacted with a base and a second monomer 613. The second monomer 613 is a compound with at least two hydroxyl (OH) groups or at least two amino ($NH_2$) groups (e.g., a diol, polyol, diamine, polyamine, etc.). These compounds 613 are illustrated as a shaded circle with attached W groups. Examples of bases that can be used as initiators include potassium hydroxide (KOH), sodium hydroxide (NaOH), lithium hydroxide (LiOH), 1,8-diazabicyclo[5.4.0]undec-7-ene (DBU), and triazabicyclodecene (TBD). The W group represents a hydroxyl group or an amino group. It should be noted that, while two W groups are illustrated herein, there are more than two W groups in some embodiments. The reaction may be performed neat or in an amount of solvent (e.g., chloroform or THF) to dissolve the components of the reaction mixture. The reaction is monitored by TLC. Standard procedures for quenching, solvent removal, and purification are performed to give the epoxy-derived flame-retardant limonene-based polymers. Molecular weight ranges of the total composition could be between about 1,000 g/mol to about 1,000,000 g/mol.

Additionally, in some embodiments, the difunctionalized limonene-based flame-retardant compounds 604 (i.e., 405 (CL1) and 505 (CL7)) having epoxy R-groups self-polymerizes under basic conditions. In these instances, the reaction does not include the second monomer 613. Suitable bases and solvents are provided above. The reaction is monitored by TLC. Standard procedures for quenching, solvent removal, and purification are performed to give the epoxy-derived flame-retardant limonene-based polymers. Molecular weight ranges of the total composition could be between about 1,000 g/mol to about 1,000,000 g/mol.

In method 610b, alkenyl (e.g., allyl- and vinyl-) derived limonene-based flame-retardant polymers 610a (P2) and 610b (P8) are formed from difunctionalized limonene-based flame-retardant monomers 405 (CL1) and 505 (CL7) having alkenyl R groups 604, respectively. As an example, the difunctionalized limonene-based flame-retardant compound 410 (CL2) is reacted with a Ziegler-Natta catalyst. Ziegler-Natta catalysts catalyze the polymerization of 1-alkenes. Examples of these catalysts can include heterogeneous Ziegler-Natta catalysts based on titanium compounds and homogeneous Ziegler-Natta catalysts based on complexes of titanium, zirconium, or hafnium. Heterogeneous and homogeneous Ziegler-Natta catalysts can be used in combination with organoaluminum co-catalysts in some embodiments.

The polymerization using Ziegler-Natta catalysts may be carried out in any common reactor suitable for the polymerization of alk-1-enes, either batchwise or, preferably, continuously, i.e., in solution, as suspension polymerization including the bulk polymerization in liquid monomer or as gas phase polymerization. Examples of suitable reactors include continuously operated stirred reactors, loop reactors, fluid bed reactors, or horizontal or vertical stirred powder bed reactors. It will be understood that the polymerization may be carried out in a series of consecutively coupled reactors. The reaction time depends on the chosen reaction conditions. In general, the reaction time is from about 0.2 to about 20 hours, usually from about 0.5 to about 10 hours most preferably between 0.5 and 2 hours.

In general the polymerization with Ziegler-Natta catalysts is carried out at a temperature in the range of from about 20° C. to about 150° C., preferably from about 50° C. to about 120° C., and more preferably from about 60° C. to about 95° C., and a pressure in the range of from about 1 to 100 bar, preferably from about 15 to about 50 bar, and more preferably from about 20 to about 45 bar. The molecular weight of the resulting polymers may be controlled and adjusted over a wide range by adding polymer chain transfer or -termination agents as commonly used in the art of polymerization, such as hydrogen. In addition an inert solvent, such as toluene or hexane, or an inert gas, such as nitrogen or argon, and smaller amounts of a powdered polymer may be added. Molecular weight ranges of the total composition could be between about up to about 2,000,000 g/mol (approximately 77,000 repeat units).

In method 610c, carbonate-derived limonene-based flame-retardant polymers 615a (P3) and 615b (P4) are formed from difunctionalized limonene-based flame-retardant monomers 415 (CL3) and 515 (CL9) having carbonate R groups 604, respectively. As an example, the difunctionalized limonene-based flame-retardant monomer 415 (CL3) is reacted in a ring-opening polymerization initiated by a base. Examples of bases that can be used as initiators include potassium hydroxide (KOH), sodium hydroxide (NaOH), lithium hydroxide (LiOH), 1,8-diazabicyclo[5.4.0]undec-7-ene (DBU), and triazabicyclodecene (TBD). The reaction may be performed neat, or in an amount of solvent (e.g., THF, 1,4-dioxane, chloroform, toluene, dimethylformamide (DMF), chlorobenzene, and methyl-tertbutyl ether) sufficient to dissolve the reaction components. The reaction is monitored by TLC. Standard procedures for quenching, solvent removal, and purification are performed to give the carbonate-derived limonene-based flame-retardant polymers. Molecular weight ranges of the total composition could be between about 1,000 g/mol to about 1,000,000 g/mol.

In addition to the polymers illustrated in FIG. 6B, the limonene-based flame-retardant compounds disclosed herein can be used in the synthesis of other flame-retardant polymers in some embodiments. In such embodiments, the limonene-based flame-retardant compound is incorporated into the polymer by chemically bonding the limonene-based flame-retardant compound to one or more polymer chains. An array of classes of flame-retardant polymers can be made with different combinations of monomers. These polymerization methods are in accordance with polymer chemistry platforms that can include epoxy resins, polyhydroxylurethanes (PHUs), polycarbonates, polymers obtained by radical polymerization, polyurethanes (PUs), polyesters, polyacrylates, polyimides, polyureas, polyamides, poly(vinylesters).

Moreover, the limonene-based flame-retardant compounds, monomers, and polymers described herein can be blended with polymeric materials by any technique known in the art, including twin-screw compounding, extrusion (i.e., reactive extrusion, hot melt extrusion), and solvent coating/casting. Such techniques, among others, are known to those skilled in the art.

One example of an application of polymers that incorporate limonene-based flame-retardant compounds is in plastics used in electronics hardware, such as integrated circuit packages. Additional applications can include acoustic dampening, cushioning, plastics, synthetic fibers, insulation, etc. The limonene-based flame-retardant compounds can also be used to make adhesives such as bio-adhesives, elastomers, thermoplastics, emulsions, thermosets, etc. Further, materials containing the limonene-based flame-retardant compounds can be incorporated into various devices with electronic components that can include printed circuit boards (PCBs), semiconductors, transistors, optoelectronics, capacitors, resistors, and chip carriers.

Resins for printed circuit boards (PCBs) can be made flame retardant by incorporating polymers that include limonene-based flame-retardant compounds. PCBs are electrical circuits that can be found in most types of electronic device, and they support and electronically connect electrical components in the device. PCBs are formed by etching a copper conductive layer laminated onto an insulating substrate. The insulating substrate can be a laminate comprising a resin and a fiber. Many resins in PCBs contain a polymer, such as an epoxy, a polyhydroxyurethane, a polycarbonate, a polyester, a polyacrylate, a polyimide, a polyamide, a polyurea, a poly(vinyl-ester), a polyphenylene oxide, a bismaleimide triazine, and combinations thereof. Using polymers that incorporate the limonene-based flame-retardant compounds can prevent the PCB from catching fire when exposed to high temperature environments or electrical power overloads.

The descriptions of the various embodiments of the present disclosure have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

While the foregoing is directed to embodiments of the present invention, other and further embodiments of the invention may be devised without departing from the basic scope thereof, and the scope thereof is determined by the claims that follow.

What is claimed is:

1. A limonene-based flame-retardant compound having the structure

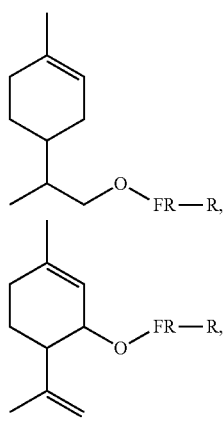

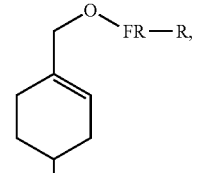

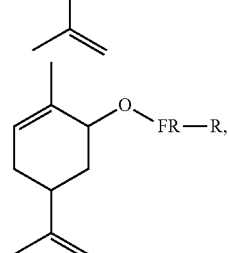

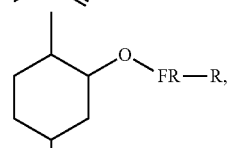

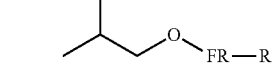

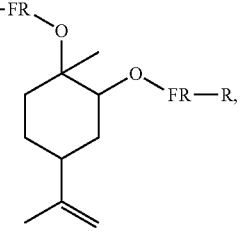

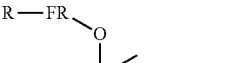

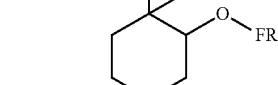

wherein:
each FR includes a phosphonate group; and
each R is independently alkyl or substituted alkyl.

2. The limonene-based flame-retardant compound of claim 1, wherein the substituted alkyl includes an alkene functional group.

3. The limonene-based flame-retardant compound of claim 1, wherein the substituted alkyl includes an epoxide functional group.

4. The limonene-based flame-retardant compound of claim 1, wherein the substituted alkyl includes a carbonate functional group.

5. The limonene-based flame-retardant compound of claim 1, wherein the substituted alkyl includes one or more of

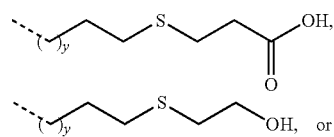

-continued

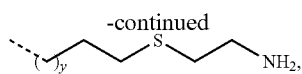

wherein:
y is an integer between 1 and 12, and
the dotted line bond indicates a connection to the phosphonate group.

6. The limonene-based flame-retardant compound of claim 1, wherein is a hydroxyl-functionalized limonene.

7. The limonene-based flame-retardant compound of claim 5, wherein y is 1.

8. The limonene-based flame-retardant compound of claim 1, wherein the substituted alkyl is

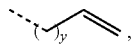

wherein:
y is an integer between 1 and 12, and
the dotted line bond indicates a connection to the phosphonate group.

9. The limonene-based flame-retardant compound of claim 1, wherein the substituted alkyl is

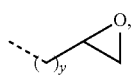

wherein:
y is an integer between 1 and 12, and
the dotted line bond indicates a connection to the phosphonate group.

10. The limonene-based flame-retardant compound of claim 1, wherein the substituted alkyl is

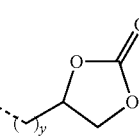

wherein:
y is an integer between 1 and 12, and
the dotted line bond indicates a connection to the phosphonate group.

11. A limonene-based flame-retardant compound having the structure

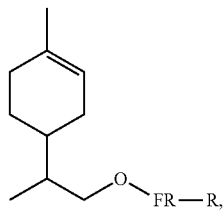

-continued

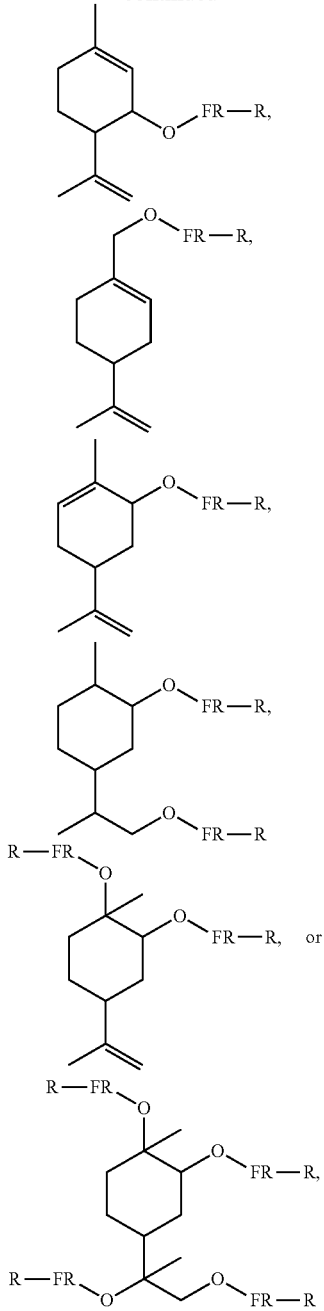

wherein:
each FR includes a phosphate group or a phosphonate group; and
each R is independently

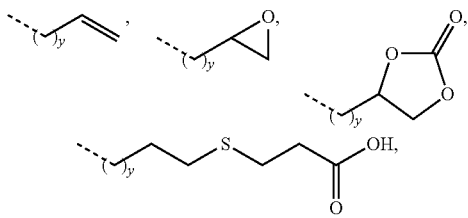

-continued

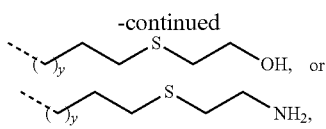

wherein:
y is an integer between 1 and 12, and
the dotted line bond indicates a connection to the phosphate group or phosphonate group.

12. The limonene-based flame-retardant compound of claim 11, wherein y is 1.

13. The limonene-based flame-retardant compound of claim 11, wherein FR is the phosphate group.

14. The limonene-based flame-retardant compound of claim 11, wherein FR is the phosphonate group.

15. A limonene-based flame-retardant compound having the structure

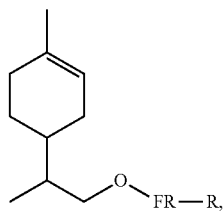

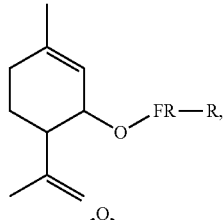

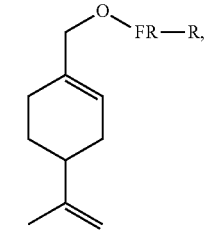

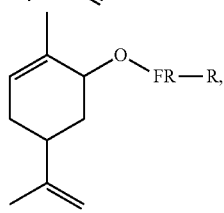

-continued

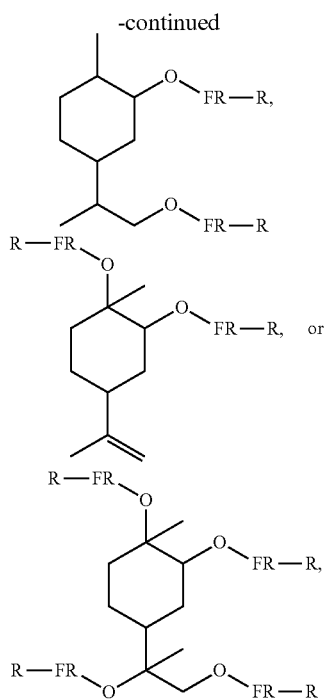

wherein:
each FR includes a phosphate group; and
each R is independently

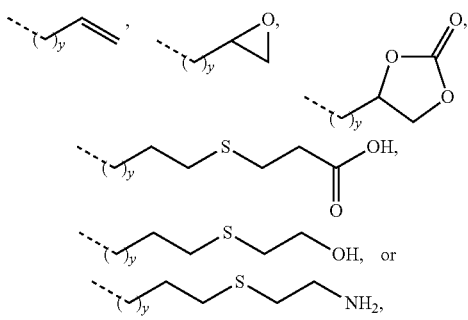

wherein:
y is an integer between 1 and 12, and
the dotted line bond indicates a connection to the phosphate group or phosphonate group.

16. The limonene-based flame-retardant compound of claim 15, wherein y is 1.

* * * * *